United States Patent
Jones et al.

(10) Patent No.: US 11,191,760 B2
(45) Date of Patent: Dec. 7, 2021

(54) **COMPOSITIONS AND METHODS FOR TREATING *HELICOBACTER PYLORI* INFECTION**

(71) Applicant: The Hospital for Sick Children, Toronto (CA)

(72) Inventors: Nicola Jones, Whitby (CA); Laura Greenfield, Vaughan (CA); Mariana Capurro, Toronto (CA)

(73) Assignee: The Hospital for Sick Children, Toronto (CA)

( * ) Notice: Subject to any disclaimer, the term of this patent is extended or adjusted under 35 U.S.C. 154(b) by 94 days.

(21) Appl. No.: 16/091,173

(22) PCT Filed: Apr. 6, 2017

(86) PCT No.: PCT/CA2017/050420
§ 371 (c)(1),
(2) Date: Oct. 4, 2018

(87) PCT Pub. No.: WO2017/173544
PCT Pub. Date: Oct. 12, 2017

(65) Prior Publication Data
US 2020/0016146 A1 Jan. 16, 2020

Related U.S. Application Data

(60) Provisional application No. 62/319,035, filed on Apr. 6, 2016.

(51) Int. Cl.
*A61K 31/445* (2006.01)
*A61K 31/4709* (2006.01)
*A61K 31/18* (2006.01)
*A61K 31/4535* (2006.01)
*A61K 45/06* (2006.01)

(52) U.S. Cl.
CPC .......... *A61K 31/4709* (2013.01); *A61K 31/18* (2013.01); *A61K 31/4535* (2013.01); *A61K 45/06* (2013.01)

(58) Field of Classification Search
CPC .................................................. A61K 31/445
USPC ....................................................... 514/323
See application file for complete search history.

(56) References Cited

FOREIGN PATENT DOCUMENTS

WO 2015118167 8/2015

OTHER PUBLICATIONS

Chandra et al. "A role for the Ca2+ channel TRPML1 in gastric acid secretion, based on analysis of knockout mice" Gastroenterology, 140(3):857-867 (2011).
Cheng et al. "Mucolipins: Intracellular TRPML1-3 Channels" FEBS Letters, 584(10):2013-2021 (2010).
Dong et al. "PI(3,5)P2 controls membrane trafficking by direct activation of mucolipin Ca2+ release channels in the endolysosome" Nature Communications, 1(38):1-11 (2010).
Grimm et al. "Small molecule activators of TRPML3" Cell Chemical Biology, 17(2):135-148 (2010).
Kim et al. "Remodeling the host environment: modulation of the gastric epithelium by the Helicobacter pylori vacuolating toxin (VacA)" Frontiers in Cellular and Infection Microbiology, 2(37):1-18 (2012).
Kiselyov et al. "The intracellular Ca2+ channels of membrane traffic" Channels, 6(5):344-351 (2012).
Palframan et al. "Vacuolating cytotoxin A (VacA), a key toxin for Helicobacter pylori pathogenesis" Frontiers in Cellular and Infection Microbiology, 2(92):1-9 (2012).
Raju et al. "Vacuolating Cytotoxin and Variants in Atg16L1 that Disrupt Autophagy Promote Helicobacter pylori Infection in Humans" Gastroenterology, 142(5):1160-1171 (2012).
Rey-Jurado et al. "Contribution of autophagy to antiviral immunity" FEBS Letters, 589:3461-3470 (2015).
Terebiznik et al. "Helicobacter pylori VacA Toxin Promotes Bacterial Intracellular Survival in Gastric Epithelial Cells" Infection and Immunity, 74(12):6599-6614 (2006).
Terebiznik et al. "Effect of Helicobacter pylori's vacuolating cytotoxin on the autophagy pathway in gastric epithelial cells" Autophagy, 5(3):370-379 (2009).
Tombola et al. "Helicobacter pylori vacuolating toxin forms anion-selective channels in planar lipid bilayers: possible implications for the mechanism of cellular vacuolation" Biophysical Journal, 76:1401-1409 (1999).
Vergarajauregui et al. "Autophagic dysfunction in mucolipidosis type IV patients" Human Molecular Genetics, 17(17):2723-2737 (2008).
Winchell et al. "Dining In: Intracellular Bacterial Pathogen Interplay with Autophagy" Current Opinion in Microbiology, 29:9-14 (2016).
Wroblewski et al. "Helicobacter pylori and Gastric Cancer: Factors That Modulate Disease Risk" Clinical Microbiology Reviews, 23(4):713-739 (2010).
Xu et al. "Lysosomal Physiology" Annual Review of Physiology, 77:57-80 (2015).

*Primary Examiner* — Raymond J Henley, III
(74) *Attorney, Agent, or Firm* — Myers Bigel, P.A.

(57) ABSTRACT

A method for treating and/or preventing VacA+ *H. pylori* infection and a disorder associated with VacA+ *H. pylori* infection is provided. The method comprises the administration of TRPML agonists such as ML-SA1, SF-22, SF-51, MK6-83 and their derivatives.

7 Claims, 13 Drawing Sheets

COMPOSITIONS AND METHODS FOR TREATING *HELICOBACTER PYLORI* INFECTION

FIELD

The present invention relates to infections. More specifically, the present invention is, in aspects, concerned with *H. pylori* infections and compositions and methods for treating the infections and associated diseases and conditions.

BACKGROUND

International Patent Application Publication No. WO 2015/118167 relates to the use of modulators of TRPML1 for modulating cell migration, in particular, the migration of dendritic cells and tumor cells, especially for antitumoral vaccination, autoimmune disease treatment, and metastasis prevention. It is described that inhibitors of TRPML1 can be used to treat cancer, in particular to prevent or decrease metastasis. Activators of TRPML1 are suggested to be useful for mobilizing dendritic cells.

International Patent Application Publication No. WO 2012/012498 describes methods for treating or preventing a respiratory infection, including a respiratory infection caused *H. pylori*, by administering an effective amount of a TRP agonist. Treatment of the gastric mucosa is mentioned, however, treatment of respiratory viral infections is the primary and exemplified focus. Furthermore, TRMPL1 is mentioned as a channel gene found in Calu-3 lung adenocarcinoma cells and NHBE normal human bronchial epithelial cells, however, TRPV4, TRPV1, TRPA1, TRPM8, TRPV3, and TRPC6 were identified as TRP channels involved in the antiviral effects of the TRP agonists.

There is a need for alternative therapies to overcome or mitigate at least some of the deficiencies of the prior art.

SUMMARY

In accordance with an aspect, there is provided a method for treating and/or preventing a disorder associated with disrupted autophagosome maturation, the method comprising administering an agent that promotes autophagosome maturation.

In an aspect, the disorder is selected from an infection, cancer, gastritis, and peptic ulcer disease.

In an aspect, the disorder is an infection caused by bacteria or viruses selected from *Helicobacter pylori, Salmonella typhimurium, Listeria, Shigella, Legionella pneumophila, Staphylococcus aureus, Mycobacterium tuberculosis,* Group A *Streptococcus*, Epstein-Barr virus (EBV), Hepatitis B and C, human immunodeficiency virus, herpes simplex virus, influenza virus, coronaviridae family, human respiratory syncytial virus, and cytomegalovirus.

In an aspect, the disorder is an infection caused by bacteria that secrete a pore-forming toxin.

In an aspect, the bacteria are *H. pylori*.

In an aspect, the *H. pylori* is VacA$^+$.

In an aspect, the agent is selected from the group consisting of a small molecule, a peptide, an antibody, an expression construct, and combinations thereof.

In an aspect, the agent is a TRP agonist.

In an aspect, the TRP agonist is a TRPML agonist.

In an aspect, the TRPML agonist is selected from a TRPML1 agonist, a TRPML2 agonist, a TRPML3 agonist, or a combination thereof.

In an aspect, the agonist is specific for one or more TRP channels.

In an aspect, the agonist is specific for TRPML1 and/or TRPML3.

In an aspect, the agonist is selected from the group consisting of ML-SA1, SF-22, SF-51, MK6-83, derivatives thereof, prodrugs thereof, analogs thereof, and combinations thereof.

In an aspect, the agent is administered in combination with an antibiotic.

In an aspect, the combination shows a synergistic treatment and/or preventative effect.

In accordance with another aspect, there is provided a composition for treating and/or preventing a disorder associated with disrupted autophagosome maturation, the composition comprising an agent that promotes autophagosome maturation.

In an aspect, the composition further comprises an antibiotic.

In an aspect, the agent and the antibiotic are in synergistic amounts.

In an aspect, the disorder is selected from an infection, cancer, gastritis, and peptic ulcer disease.

In an aspect, the disorder is an infection caused by bacteria or viruses selected from *Helicobacter pylori, Salmonella typhimurium, Listeria, Shigella, Legionella pneumophila, Staphylococcus aureus, Mycobacterium tuberculosis,* Group A *Streptococcus*, Epstein-Barr virus (EBV), hepatitis B and C virus, human immunodeficiency virus, herpes simplex virus, influenza virus, coronaviridae family, human respiratory syncytial virus, and cytomegalovirus.

In an aspect, the disorder is an infection caused by bacteria that secrete a pore-forming toxin.

In an aspect, the bacteria are *H. pylori*.

In an aspect, the *H. pylori* is VacA$^+$.

In an aspect, the agent is selected from the group consisting of a small molecule, a peptide, an antibody, an expression construct, and combinations thereof.

In an aspect, the agent is a TRP agonist.

In an aspect, the TRP agonist is a TRPML agonist.

In an aspect, the TRPML agonist is selected from a TRPML1 agonist, a TRPML2 agonist, a TRPML3 agonist, or a combination thereof.

In an aspect, the agonist is specific for one or more TRP channels.

In an aspect, the agonist is specific for TRPML1 and/or TRPML3.

In an aspect, the agonist is selected from the group consisting of ML-SA1, SF-22, SF-51, MK6-83, derivatives thereof, prodrugs thereof, analogs thereof, and combinations thereof.

In accordance with an aspect, there is provided a kit for treating and/or preventing a disorder associated with disrupted autophagosome maturation, the kit comprising an agent that promotes autophagosome maturation.

In an aspect, the kit further comprises an antibiotic.

In an aspect, the agent and the antibiotic are in synergistic amounts.

In an aspect, the disorder is selected from an infection, cancer, gastritis, and peptic ulcer disease.

In an aspect, the disorder is an infection caused by bacteria or viruses selected from *Helicobacter pylori, Salmonella typhimurium, Listeria, Shigella, Legionella pneumophila, Staphylococcus aureus, Mycobacterium tuberculosis,* Group A *Streptococcus*, Epstein-Barr virus (EBV), hepatitis B and C virus, human immunodeficiency virus, herpes simplex virus, influenza virus, coronaviridae family, human respiratory syncytial virus, and cytomegalovirus.

In an aspect, the disorder is an infection caused by bacteria that secrete a pore-forming toxin.

In an aspect, the bacteria are *H. pylori*.

In an aspect, the *H. pylori* is VacA⁺.

In an aspect, the agent is selected from the group consisting of a small molecule, a peptide, an antibody, an expression construct, and combinations thereof.

In an aspect, the agent is a TRP agonist.

In an aspect, the TRP agonist is a TRPML agonist.

In an aspect, the TRPML agonist is selected from a TRPML1 agonist, a TRPML2 agonist, a TRPML3 agonist, or a combination thereof.

In an aspect, the agonist is specific for one or more TRP channels.

In an aspect, the agonist is specific for TRPML1 and/or TRPML3.

In an aspect, the agonist is selected from the group consisting of ML-SA1, SF-22, SF-51, MK6-83, derivatives thereof, prodrugs thereof, analogs thereof, and combinations thereof.

In accordance with an aspect, there is provided a method for rendering *H. pylori* susceptible to antibiotic treatment and/or immune system attack, the method comprising administering a TRPML agonist.

In accordance with an aspect, there is provided a method for exposing intracellular bacteria to an extracellular environment, comprising administering a TRPML agonist.

In accordance with an aspect, there is provided a method for treating a VacA⁺ *H. pylori* infection, the method comprising administering a TRPML agonist.

In accordance with an aspect, there is provided a a method for rendering *H. pylori* susceptible to antibiotic treatment and/or immune system attack, the method comprising administering an agent that promotes autophagosome maturation.

In an aspect, the *H. pylori* is VacA⁺.

In an aspect, the agent is selected from the group consisting of a small molecule, a peptide, an antibody, an expression construct, and combinations thereof.

In an aspect, the agent is a TRP agonist.

In an aspect, the TRP agonist is a TRPML agonist.

In an aspect, the TRPML agonist is selected from a TRPML1 agonist, a TRPML2 agonist, a TRPML3 agonist, or a combination thereof.

In an aspect, the agonist is specific for one or more TRP channels.

In an aspect, the agonist is specific for TRPML1 and/or TRPML3.

In an aspect, the agonist is selected from the group consisting of ML-SA1, SF-22, SF-51, MK6-83, derivatives thereof, prodrugs thereof, analogs thereof, and combinations thereof.

In an aspect, the agent is administered in combination with an antibiotic.

In an aspect, the combination shows a synergistic treatment and/or preventative effect.

In accordance with an aspect, there is provided a method for exposing intracellular bacteria to an extracellular environment, comprising administering an agent that promotes autophagosome maturation.

In an aspect, the bacteria is selected from *Helicobacter pylori, Salmonella typhimurium, Listeria, Shigella, Legionella pneumophila, Staphylococcus aureus, Mycobacterium tuberculosis*, and Group A *Streptococcus*.

In an aspect, the bacteria secrete a pore-forming toxin.

In an aspect, the bacteria are *H. pylori*.

In an aspect, the *H. pylori* is VacA⁺.

In an aspect, the agent is selected from the group consisting of a small molecule, a peptide, an antibody, an expression construct, and combinations thereof.

In an aspect, the agent is a TRP agonist.

In an aspect, the TRP agonist is a TRPML agonist.

In an aspect, the TRPML agonist is selected from a TRPML1 agonist, a TRPML2 agonist, a TRPML3 agonist, or a combination thereof.

In an aspect, the agonist is specific for one or more TRP channels.

In an aspect, the agonist is specific for TRPML1 and/or TRPML3.

In an aspect, the agonist is selected from the group consisting of ML-SA1, SF-22, SF-51, MK6-83, derivatives thereof, prodrugs thereof, analogs thereof, and combinations thereof.

In an aspect, the agent is administered in combination with an antibiotic.

In an aspect, the combination shows a synergistic effect.

In accordance with an aspect, there is provided a method for treating and/or preventing an infection caused by an intracellular bacteria, comprising administering a TRPML agonist to a subject in need thereof.

In an aspect, the bacteria is selected from *Helicobacter pylori, Salmonella typhimurium, Listeria, Shigella, Legionella pneumophila, Staphylococcus aureus, Mycobacterium tuberculosis*, and Group A *Streptococcus*.

In an aspect, the bacteria secrete a pore-forming toxin.

In an aspect, the bacteria are *H. pylori*.

In an aspect, the *H. pylori* is VacA⁺.

In an aspect, the agent is selected from the group consisting of a small molecule, a peptide, an antibody, an expression construct, and combinations thereof.

In an aspect, the agent is a TRP agonist.

In an aspect, the TRP agonist is a TRPML agonist.

In an aspect, the TRPML agonist is selected from a TRPML1 agonist, a TRPML2 agonist, a TRPML3 agonist, or a combination thereof.

In an aspect, the agonist is specific for one or more TRP channels.

In an aspect, the agonist is specific for TRPML1 and/or TRPML3.

In an aspect, the agonist is selected from the group consisting of ML-SA1, SF-22, SF-51, MK6-83, derivatives thereof, prodrugs thereof, analogs thereof, and combinations thereof.

In an aspect, the agent is administered in combination with an antibiotic.

In an aspect, the combination shows a synergistic treatment and/or preventative effect.

Other features and advantages of the present invention will become apparent from the following detailed description. It should be understood, however, that the detailed description and the specific examples while indicating embodiments of the invention are given by way of illustration only, since various changes and modifications within the spirit and scope of the invention will become apparent to those skilled in the art from said detailed description.

DESCRIPTION OF THE FIGURES

The present invention will be further understood from the following description with reference to the Figures, in which.

DETAILED DESCRIPTION

Figure 1:
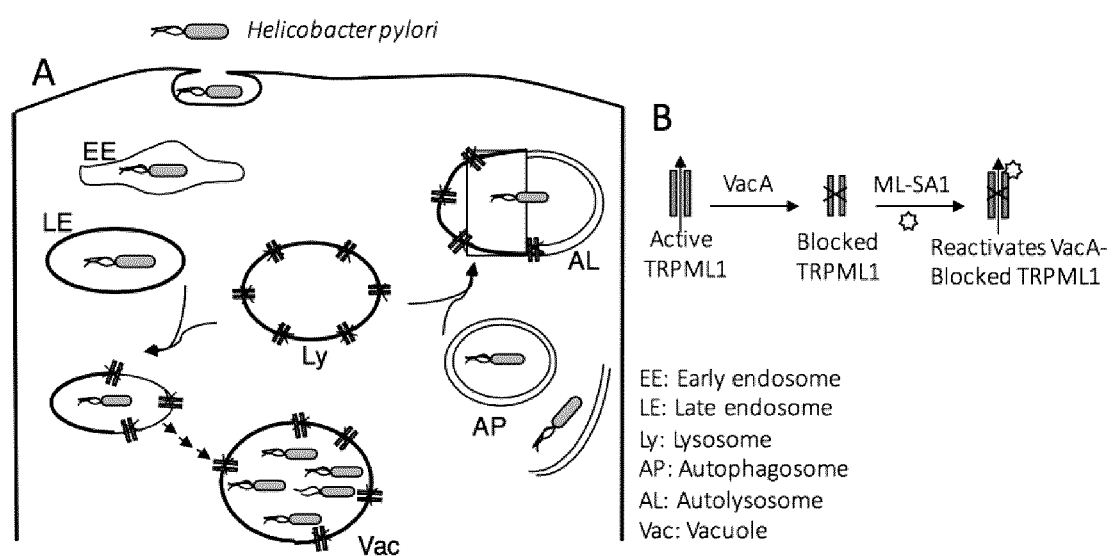
FIG. 1 is a schematic model, showing that infection with a VacA+ *H. pylori* strain impairs TRPML1, which is important for the vesicular trafficking required to eliminate the intracellular bacteria as well as for proper autophagy (1A). It was further established that the TRPML1 agonist ML-SA1 overcomes the effect of VacA on TRPML1 (1B), reversing the vesicular trafficking defects and inhibiting bacterial colonization.

The autophagy pathway is a highly conserved pathway in which cytoplasmic contents including damaged proteins, organelles and invading pathogens or toxins are enveloped in an autophagosome which then fuses with a lysosome, resulting in degradation of the contents. Thus autophagy serves as a host response to promote cellular homeostasis and protect cells against invading pathogens. As such several pathogens have developed mechanisms to subvert the pathway including bacteria (e.g. *Helicobacter pylori, Salmonella typhimurium, Listeria, Shigella, Legionella pneumophila, Staphylococcus aureus, Mycobacterium tuberculosis*, and Group A *Streptococcus*) (*Curr Opin Microbiol* 2016; 29:9-14) and viruses (hepatitis B and C, human immunodeficiency virus, herpes simplex virus, influenza virus, coronaviridae family, human respiratory syncytial virus, cytomegalovirus, and Epstein-Barr virus (EBV)) (*FEBS Lett* 2015; 589: 3461-70). Furthermore, current evidence suggests that autophagy plays a role in tumorigenesis. Therefore, during chronic infection, microbial manipulation of autophagy could create a pro-tumorigenic environment. Thus the development of therapies to counter pathogenic mechanisms to subvert autophagy are of great interest.

*Helicobacter pylori* is a gastric pathogen that colonizes roughly half of the world's population (Wroblewski et al. (2010) *Clin Microbiol Rev* 23:713-739). Infection with the bacterium causes chronic gastritis in all infected individuals, while a subset of individuals will develop more serious complications such as peptic ulcer disease, and gastric cancers including lymphoma and adenocarcinoma. Gastric cancer represents a significant global health burden, serving as the third leading cause of cancer-related deaths worldwide (Ferlay et al. (2013) GLOBOCAN 2012 v1.0, Cancer Incidence and Mortality Worldwide: IARC CancerBase No. 11, Lyon, France: International Agency for Research on Cancer). Unfortunately, the prognosis is poor, illustrated by a survival rate of less 25% in Canada (Canadian Cancer Society's Advisory Committee on Cancer Statistics (2014) *Canadian Cancer Statistics* 2014. Toronto, ON: Canadian Cancer Society). As *H. pylori* infection is considered the strongest known risk factor for the development of gastric cancer, a comprehensive understanding of the bacteria's pathogenesis is urgently required.

A major virulence determinant of *H. pylori* is the vacuolating cytotoxin (VacA). VacA promotes colonization and is associated with more severe disease, including cancer (Kim and Blanke (2012) *Front Cell Infect Microbiol* 2:37). The toxin is secreted by the bacteria and inserted into host membranes where it forms chloride-specific membrane channels (Tombola et al. (1999) *Biophys J* 76:1401-1409; Palframan et al. (2012) *Front Cell Infect Microbiol* 2:92). The effects of VacA infection are numerous. VacA promotes the formation of large, non-degradative intracellular vacuoles wherein *H. pylori* can reside (Terebiznik et al. (2006) *Infect Immun* 74:6599-6614). VacA also disrupts the host's autophagy pathway, which plays a critical role in controlling infection (Terebiznik et al. (2009) *Autophagy* 5:370-379). Together these effects confer a significant survival advantage of VacA$^+$ *H. pylori* over VacA$^-$ strains (Terebiznik et al. (2006) *Infect Immun* 74:6599-6614; Raju et al. (2012) *Gastroenterology* 142:1160-1171). The unique intracellular niche permits VacA$^+$ *H. pylori* to evade the host's immune system and potentially avoid exposure to antibiotics. Importantly, current treatments for *H. pylori* are not aimed at elimination of intracellular bacteria, which may serve as a reservoir for re-infection following existing treatment regimes.

The formation of large vacuoles and disrupted autophagy by VacA indicate that the toxin impairs the host's endosome trafficking system. In healthy cells, extracellular material is engulfed by endocytosis and trafficked through different vacuolar compartments that eventually fuse with the lysosome to degrade its contents. Lamp1 is a protein used to identify late endosomes/lysosomes. In a similar process, intracellular material and invading pathogens are engulfed by a double membrane bound vacuole called the autophagosome, which also fuses with the lysosome for degradation. During autophagy, a cytosolic protein called LC3-I becomes conjugated to the autophagosomal membrane forming LC3-II, a marker for autophagosomes. These two processes are complex and require the coordinated activity of numerous proteins as well as the establishment of specific ion gradients across vacuole membranes to signal trafficking events (Xu and Ren (2015) *Annu Rev Physiol* 77:57-80).

In VacA-treated cells, large vacuoles arise from the combined fusion of late endosomes and osmotic swelling (Tombola et al. (1999) *Biophys J* 76:1401-1409; Terebiznik et al. (2006) *Infect Immun* 74:6599-6614). These compartments, as well as autophagosomes, are non-degradative because lysosomes fail to acquire an important degradative enzyme called cathepsin D (Terebiznik et al. (2006) *Infect Immun* 74:6599-6614; Raju et al. (2012) *Gastroenterology* 142: 1160-1171). Interestingly, cells with impaired activity of the mucolipin transient receptor potential channel 1 (TRPML1; Mcoln-1) display a remarkably similar phenotype to those infected with VacA, including enlarged vacuoles and impaired autophagy (Cheng et al. (2010) *FEBS Lett* 584: 2013-2021; Vergarajauregui et al. (2008) *Hum Mol Genet* 17:2723-2737). Furthermore, in vivo, both humans with TRPML1 mutations and TRPML1−/− mice display abnormal parietal cell vacuolation and impaired gastric acid secretion, resulting in hypergastrinemia and hypochlorhydria (Chandra et al. (2011) *Gastroenterology* 140:857-867). These conditions occur during *H. pylori* infection and are associated with increased risk for gastric cancer.

TRMPL1 is a $Ca^{2+}$ channel localized primarily to late endosomes, whose impairment is consistent with an important role for $Ca^{2+}$ in endosome trafficking (Kiselyov et al. (2012) *Channels* 6:344-351). Channel activation requires an interaction with the phosphoinositide, $PI(3,5)P_2$ (Dong et al. (2010) *Nat Commun* 1:38). Deficiency in $PI(3,5)P_2$ also results in enlarged vacuoles and trafficking defects, which can be rescued by over-expression of TRPML1 (Dong et al. (2010) *Nat Commun* 1:38). However, beyond a requirement for $PI(3,5)P_2$, the mechanism of TRPML1 activation is poorly understood. Presumably, specific ion gradients and/or membrane potential are required.

As has been described above, *H. pylori* infect half of the world's human population representing a significant threat to global health. VacA is one of the main virulence factors associated with more severe disease outcomes. VacA is a multifunctional secreted toxin that oligomorizes to form a chloride-selective membrane channel. In VacA-treated cells, lysosomes fail to acquire cathepsin D and are non-degradative. Furthermore, VacA disrupts the maturation of the host's autophagy pathway and generates large vacuoles where *H. pylori* reside. This intracellular protective niche provides a significant survival advantage of VacA+ *H. pylori* strains over VacA− strains. The mechanism by which VacA alters vesicular membrane trafficking is currently unknown.

Proper vesicular trafficking depends on calcium anion levels regulated mainly through TRPML1. Interestingly, TRPML1 deficient cells display a remarkably similar phenotype to those infected with VacA, including enlarged vacuoles and disrupted autophagy. Furthermore, both TRPML1 deficient mice and humans display hypergastrinemia and hypochlorhydria, conditions observed during *H. pylori* infection in humans. In VacA− treated cells, Cl− homeostasis is disturbed, which prompted investigation of the possible impairment of TRPML1 function during infection with VacA+ *H. pylori*, based on the hypothesis that VacA impairs TRPML1 function to promote disease. The studies outlined below (see figures) identify TRPML1 as a therapeutic target for treatment of VacA+ *H. pylori* infection. These findings represent the first therapeutic target for VacA+ *H. pylori* aimed specifically at eliminating intracellular bacteria, which likely contribute most significantly to chronic infection and disease. Furthermore, restoration of vesicular trafficking and autophagy should promote cellular homeostasis and reduce the pro-tumorigenic environment.

As will be described in the Examples below, the effect of a synthetic TRPML1 agonist, ML-SA1, or TRPML1 or TRPML3 overexpression on VacA+ *H. pylori* infected gastric adenocarcinoma (AGS) cells was determined. Vacuolation, lysosomal cathepsin D levels, degradative lysosomal function, autophagy and intracellular bacterial survival were all assessed.

Treatment of VacA+ *H. pylori* infected AGS cells with 20 µM ML-SA1 reversed VacA− induced vacuolation as assessed by Lamp1 staining. ML-SA1 treatment reversed missorting of cathepsin D, leading to the recovery of lysosomal and autophagic degradative function and the elimination of the intracellular protective niche. Consistent with this, ML-SA1 treatment decreased the survival advantage of VacA+ *H. pylori* as assessed by colony forming units. Importantly, overexpression of TRPML1 or TRPML3 in AGS cells also reversed VacA-induced vacuolation and reduced VacA+ *H. pylori* survival, thereby confirming the role of TRPML1 and TRPML3.

Altogether, it is shown herein that the activation of TRPML1 and TRPML3 channels restores normal lysosomal and autophagic function and mitigates VacA-mediated toxic effects in gastric cells. Therefore, the TRP channel family has been identified as a target for the treatment and/or prevention of disorders that are characterized by disrupted autophagy. More specifically, the TRPML channel family has been identified as a target for the treatment and/or prevention of VacA+ *H. pylori* infections. Activation of one or a combination of TRPML channels is expected to reduce the virulence of highly pathogenic VacA+ *H. pylori* strains.

Definitions

As used herein, "treatment" or "therapy" is an approach for obtaining beneficial or desired clinical results. For the purposes described herein, beneficial or desired clinical results include, but are not limited to, alleviation of symptoms, diminishment of extent of disease, stabilized (i.e., not worsening) state of disease, delay or slowing of disease progression, amelioration or palliation of the disease state, and remission (whether partial or total), whether detectable or undetectable. "Treatment" and "therapy" can also mean prolonging survival as compared to expected survival if not receiving treatment or therapy. Thus, "treatment" or "therapy" is an intervention performed with the intention of altering the pathology of a disorder. Specifically, the treatment or therapy may directly prevent, slow down or otherwise decrease the pathology of a disease or disorder such as an infection, or may render the cells more susceptible to treatment or therapy by other therapeutic agents.

The terms "therapeutically effective amount", "effective amount" or "sufficient amount" mean a quantity sufficient, when administered to a subject, including a mammal, for example a human, to achieve a desired result, for example an amount effective to treat an infection. Effective amounts of the compounds described herein may vary according to factors such as the disease state, age, sex, and weight of the subject. Dosage or treatment regimes may be adjusted to provide the optimum therapeutic response, as is understood by a skilled person.

Moreover, a treatment regime of a subject with a therapeutically effective amount may consist of a single administration, or alternatively comprise a series of applications. The length of the treatment period depends on a variety of factors, such as the severity of the disease, the age of the subject, the concentration of the agent, the responsiveness of the patient to the agent, or a combination thereof. It will also be appreciated that the effective dosage of the agent used for the treatment may increase or decrease over the course of a particular treatment regime. Changes in dosage may result and become apparent by standard diagnostic assays known in the art. The compounds described herein may, in aspects, be administered before, during or after treatment with conventional therapies for the disease or disorder in question, such as an infection.

The term "subject" as used herein refers to any member of the animal kingdom, typically a mammal. The term "mammal" refers to any animal classified as a mammal, including humans, other higher primates, domestic and farm animals, and zoo, sports, or pet animals, such as dogs, cats, cattle, horses, sheep, pigs, goats, rabbits, etc. Typically, the mammal is human.

Administration "in combination with" one or more further therapeutic agents includes simultaneous (concurrent) and consecutive administration in any order.

The term "pharmaceutically acceptable" means that the compound or combination of compounds is compatible with the remaining ingredients of a formulation for pharmaceutical use, and that it is generally safe for administering to humans according to established governmental standards, including those promulgated by the United States Food and Drug Administration.

The term "pharmaceutically acceptable carrier" includes, but is not limited to solvents, dispersion media, coatings, antibacterial agents, antifungal agents, isotonic and/or absorption delaying agents and the like. The use of pharmaceutically acceptable carriers is well known.

Included herein are pharmaceutically acceptable salts, solvates and prodrugs of the compounds described herein and mixtures thereof.

The term "TRP channel" refers to a member of the TRP family of channels. TRP channels have been classified into at least six groups: TRPC (short), TRPV (vanilloid), TRPM (long, melastatin), TRPP (polycystins), TRPML (mucolipins), and TRPA (ANKTM1). The TRPC group can be divided into 4 subfamilies (TRPC1, TRPC4,5, TRPC3,6,7 and TRPC2) based on sequence homology and functional similarities. Currently the TRPV family has 6 members. TRPV5 and TRPV6 are more closely related to each other than to TRPV1, TRPV2, TRPV3, or TRPV4. TRPV3 is most closely related to TRPV4, and is more closely related to TRPV1 and TRPV2 than to TRPV5 and TRPV6. The TRPM family has 8 members. Constituents include the following: the founding member TRPM1 (Melastatin or LTRPC1), TRPM3 (KIAA1616 or LTRPC3), TRPM7 (TRP-PLIK, ChaK(1), LTRPC7), TRPM6 (ChaK2), TRPM2 (TRPC7 or LTRPC2), TRPM8 (Trp-p8 or CMR1), TRPM5 (Mtr1 or LTRPC5), and TRPM4 (FLJ20041 or LTRPC4). The sole mammalian member of the TRPA family is ANKTM1. The TRPML family consists of the mucolipins, which include TRPML1 (mucolipins 1), TRPML2 (mucolipins 2), and TRPML3 (mucolipin3). The TRPP family consists of two groups of channels: those predicted to have six transmembrane domains and those that have 11. TRPP2 (PKD2), TRPP3 (PKD2L1), TRPP5 (PKD2L2) are all predicted to have six transmembrane domains. TRPP1 (PKD1, PC1), PKD-REJ and PKD-1L1 are all thought to have 11 transmembrane domains.

A "TRP agonist" or, more specifically, a "TRPML agonist" refers to an agent that enhances activity of the TRP channel in question. For example, the agonist may cause the channel to open more frequently or it may cause the channel to open for longer periods of time. Examples of TRP agonists include those listed in International Patent Application Publication No. 2012/012498, which is incorporated herein by reference in its entirety.

TRPML1 agonists include at least ML-SA1, SF-22, SF-51, and MK6-83. TRPML2 agonists include at least SF-21 (4-chloro-N-(2-morpholin-4-ylcyclohexyl)benzenesulfonamide), SF-41 (1-(2,4-dimethylphenyl)-4-piperidin-1-ylsulfonylpiperazine), and SF-81 (4,6-dimethyl-3-(2-methylphenyl)sulfonyl-1-propan-2-ylpyridin-2-one). TRPML3 agonists include at least ML268, ML269 and the various small molecules described by Grimm et al. (2010; *Chem Biol* 17(2):135-148; incorporated herein by reference in its entirety). It will be understood that some of these agonists are not specific for any one of TRPML1, TRPML2, and TRPML3 and may activate two or three of these channels to the same or different degrees. Derivatives, prodrugs, and analogs of any TRPML agonists, including those listed above, are included herein. Such modified TRPML agonists may have varying numbers of carbons in their rings, they may include heteroatoms or substituents, they may be saturated or unsaturated, and may contain various R groups as would be understood by a skilled person. Such modified compounds could be tested for TRPML agonist activity as described herein.

For example, the structures of ML-SA1, SF-22, and SF-51 are shown below, along with various contemplated derivatives of SF-22, including MK6-83:

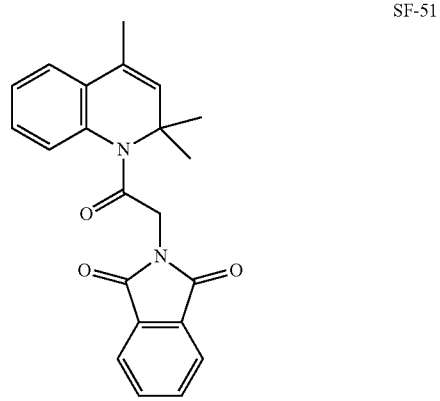

SF-51

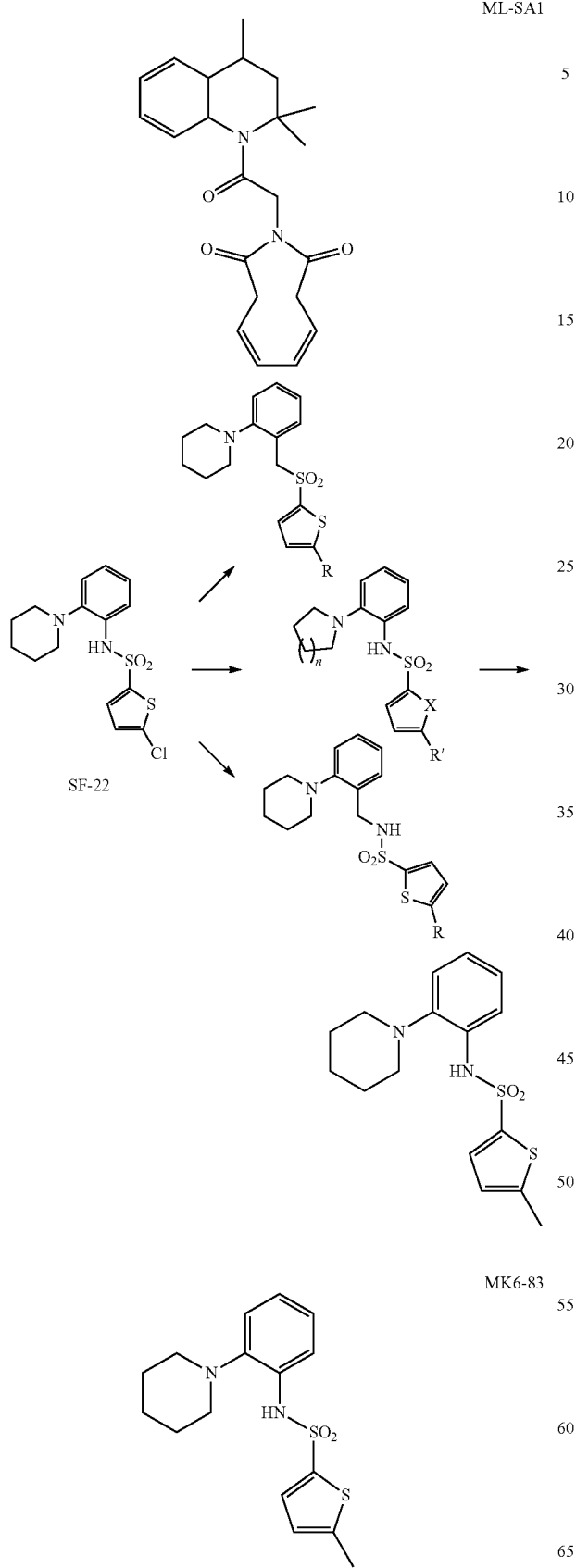
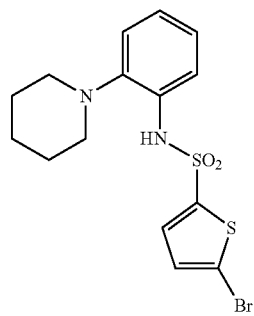
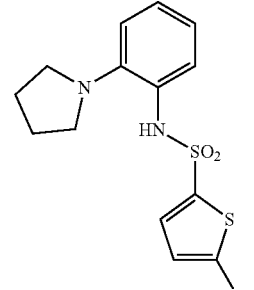
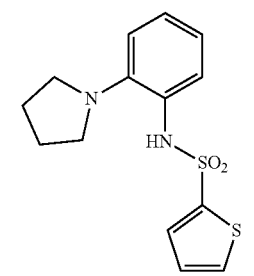
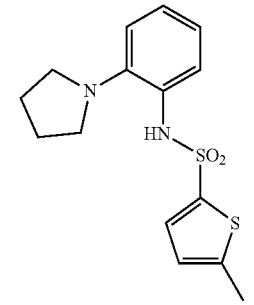
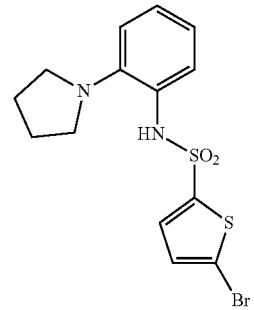

CK-06
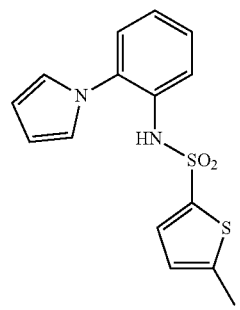
MK6-84
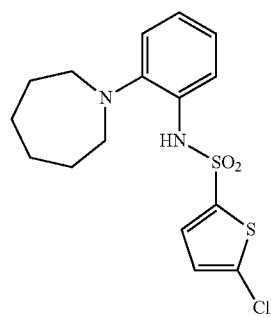
MK6-85
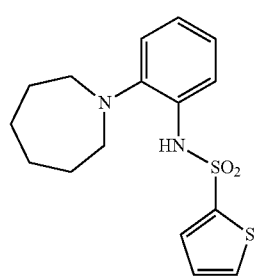
MK6-86
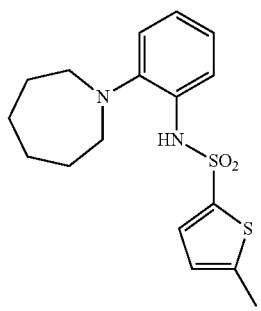
MK6-87
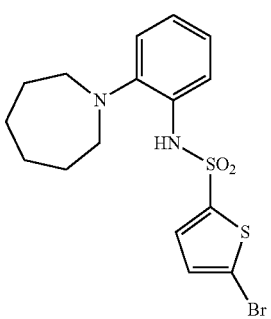
MK6-61
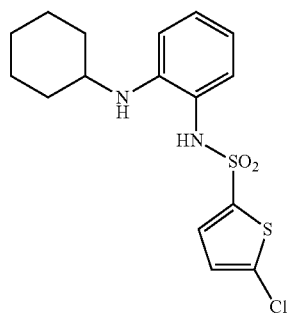
MK6-88
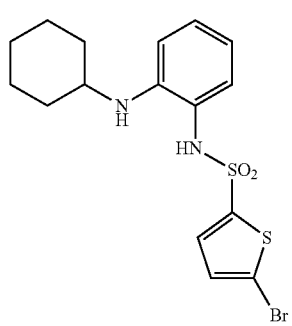
MK6-74
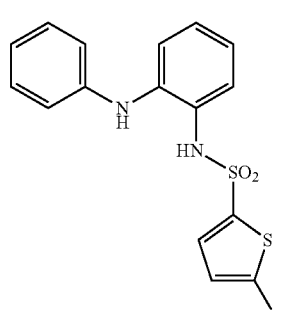
MK6-76
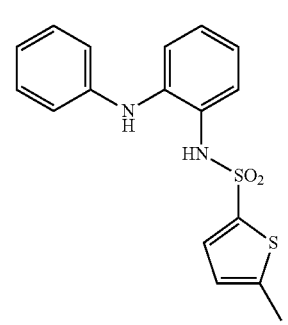
CK-07
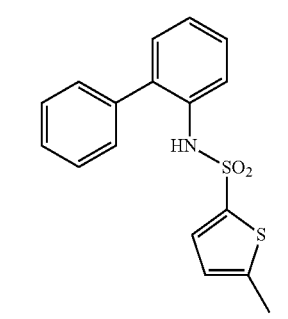

MK6-17
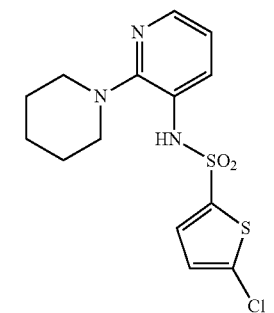
MK6-50
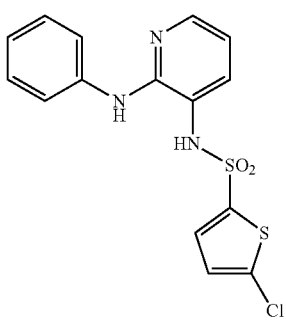
MK6-60
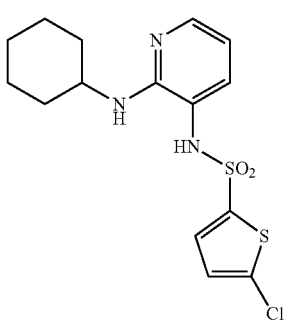
MP3-22
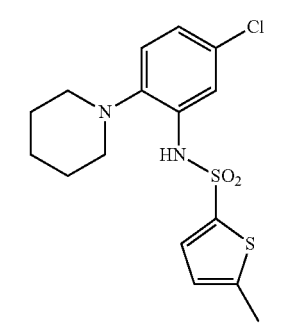
MP3-23
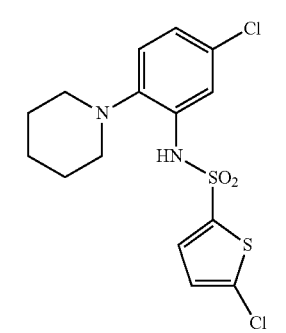
CK-19
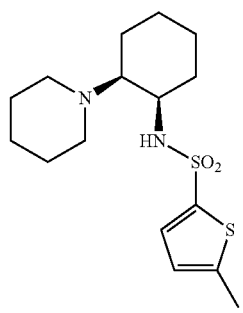
CK-20
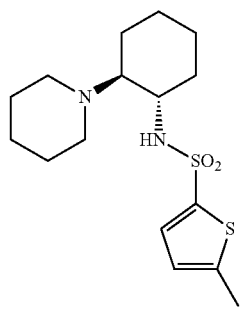
MK6-96
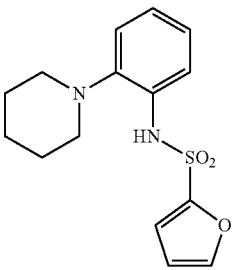
MK6-98
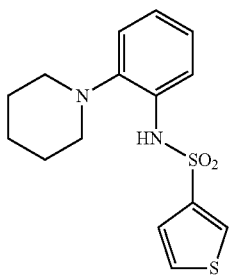
MK6-101
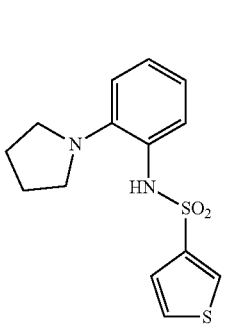

MK6-102
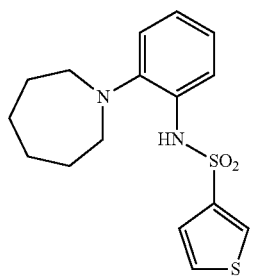
MK6-90
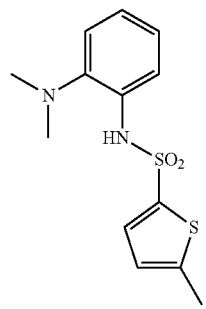
MK6-105
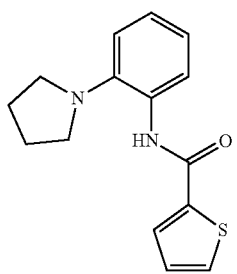
MK6-106
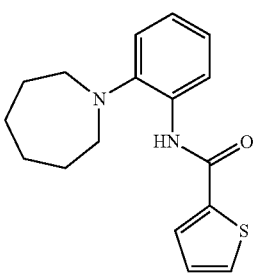
MK6-107
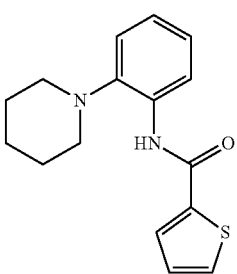
MK6-110
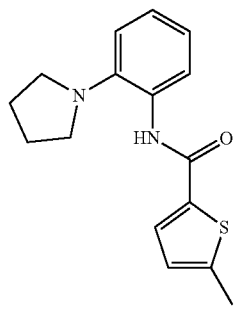
MK6-111
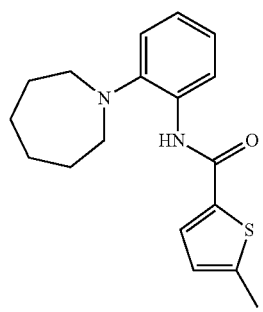
MK6-112
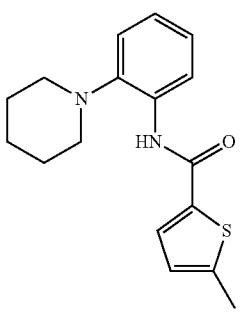
MP3-09
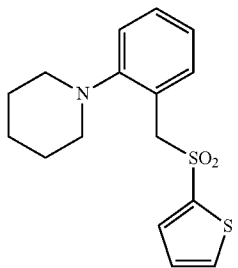
MP3-13
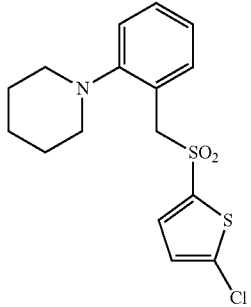

MP3-15

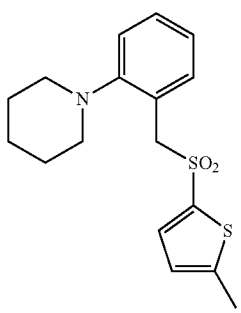

AW-251

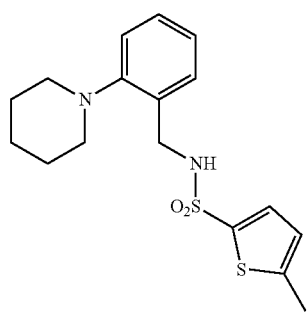

AW-252

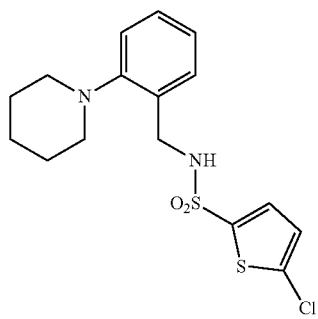

Z133963852

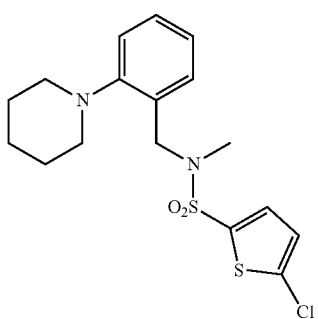

In understanding the scope of the present application, the articles "a", "an", "the", and "said" are intended to mean that there are one or more of the elements. Additionally, the term "comprising" and its derivatives, as used herein, are intended to be open ended terms that specify the presence of the stated features, elements, components, groups, integers, and/or steps, but do not exclude the presence of other unstated features, elements, components, groups, integers and/or steps. The foregoing also applies to words having similar meanings such as the terms, "including", "having" and their derivatives.

It will be understood that any aspects described as "comprising" certain components may also "consist of" or "consist essentially of," wherein "consisting of" has a closed-ended or restrictive meaning and "consisting essentially of" means including the components specified but excluding other components except for materials present as impurities, unavoidable materials present as a result of processes used to provide the components, and components added for a purpose other than achieving the technical effect(s) described herein. For example, a composition defined using the phrase "consisting essentially of" encompasses any known pharmaceutically acceptable additive, excipient, diluent, carrier, and the like. Typically, a composition consisting essentially of a set of components will comprise less than 5% by weight, typically less than 3% by weight, more typically less than 1% by weight of non-specified components.

It will be understood that any component defined herein as being included may be explicitly excluded from the claimed invention by way of proviso or negative limitation. For example, in aspects, the activation of specific TRP channels other than TRPML family member, such as TRPML1 and/or TRPML3, is explicitly excluded from the compositions and methods described herein.

In addition, all ranges given herein include the end of the ranges and also any intermediate range points, whether explicitly stated or not.

Finally, terms of degree such as "substantially", "about" and "approximately" as used herein mean a reasonable amount of deviation of the modified term such that the end result is not significantly changed. These terms of degree should be construed as including a deviation of at least ±5% of the modified term if this deviation would not negate the meaning of the word it modifies.

TRP Agonists

It will be understood that any suitable TRP agonists may be used in the compositions and methods described herein. The agonists may be specific or non-specific and can be suitably selected by a skilled person. Suitable TRP agonists include any agent that enhances activity of a TRP channel, either directly or indirectly through its action on another moiety. Examples include small molecules, peptides, antibodies, and expression constructs. A skilled person could readily test any agent and determine if it is a TRP agonist by measuring channel activity before and after treatment with the agent in question.

Typically, the TRP agonist is a TRPML agonist and, more typically, the TRPML agonist is an agonist of TRPML1, TRPML2, and/or TRPML3. More typically, the TRPML agonist is a TRPML1 agonist, such as, for example, ML-SA1, SF-22, SF-51, MK6-83, or derivatives, prodrugs, or analogs thereof.

Compositions Comprising TRP Agonists

The TRP agonists, such as TRPML agonists, described herein, in aspects, are formulated into compositions. The compositions described herein can be prepared by per se known methods for the preparation of pharmaceutically acceptable compositions that can be administered to subjects, such that an effective quantity of the active substance is combined in a mixture with a pharmaceutically acceptable vehicle. Suitable vehicles are described, for example, in Remington's Pharmaceutical Sciences (Remington's Pharmaceutical Sciences, 20th ed., Mack Publishing Company, Easton, Pa., USA, 2000). On this basis, the compositions may include, albeit not exclusively, the TRP agonists in association with one or more pharmaceutically acceptable vehicles or diluents, and may be contained in buffered solutions with a suitable pH that are iso-osmotic with physiological fluids.

Pharmaceutical compositions include, without limitation, lyophilized powders or aqueous or non-aqueous sterile injectable solutions or suspensions, which may further contain antioxidants, buffers, bacteriostats, and/or solutes that render the compositions substantially compatible with the tissues or the blood of the subject. Other components that may be present in such compositions include water, surfactants (such as Tween), alcohols, polyols, glycerin and vegetable oils, for example. Extemporaneous injection solutions and suspensions may be prepared from sterile powders, granules, tablets, or concentrated solutions or suspensions. The pharmaceutical composition may be supplied, for example, but not by way of limitation, as a lyophilized powder which is reconstituted with sterile water or saline prior to administration to the patient.

Suitable pharmaceutically acceptable carriers include essentially chemically inert and nontoxic compositions that do not interfere with the effectiveness of the biological activity of the pharmaceutical composition. Examples of suitable pharmaceutical carriers include, but are not limited to, water, saline solutions, glycerol solutions, ethanol, N-(1 (2,3-dioleyloxy)propyl)N,N,N-trimethylammonium chloride (DOTMA), diolesylphosphotidyl-ethanolamine (DOPE), and liposomes. Such compositions should contain a therapeutically effective amount of the active agent, together with a suitable amount of carrier so as to provide the form for direct administration to the patient.

Methods of Treatment and/or Prevention

As described herein, TRP agonists, such as TRPML agonists, are useful for treating and/or preventing *H. pylori* infection. They may also be useful for treating infection with other pathogens that subvert the autophagy pathway, such as, for example, *Salmonella typhimurium, Listeria, Shigella, Legionella pneumophila, Staphylococcus aureus, Mycobacterium tuberculosis*, Group A *Streptococcus*, Epstein-Barr virus (EBV), hepatitis B and C virus, human immunodeficiency virus, herpes simplex virus, influenza virus, coronaviridae family, human respiratory syncytial virus, and cytomegalovirus. Such agonists may also find use in treating other disorders that have autophagy-related pathologies that may not be pathogen-related, such as Alzheimer's disease.

It is contemplated that the TRP agonists may be used in combination with conventional treatments for *H. pylori* infection, such as antibiotics, resulting in an additive or synergistic treatment modality.

As *H. pylori* infection is a strong risk factor for gastric cancer and/or peptic ulcer disease, successful treatment of the infection also leads to prevention of gastric cancer and/or peptic ulcer disease. Therefore, TRP agonists as described herein are useful for treating infection thereby preventing a number of conditions such as gastric cancer, peptic ulcer disease, and gastritis.

The TRP agonists can, in aspects, be administered for example, by parenteral, intravenous, subcutaneous, intradermal, intramuscular, intracranial, intraorbital, ophthalmic, intraventricular, intracapsular, intraspinal, intracisternal, intraperitoneal, intranasal, intrarectal, aerosol or oral administration. Typically, the compositions described herein are administered subcutaneously, intramuscularly, or intradermally. More typically, the compositions described herein are administered orally, particularly in the case of a gastric infection.

The TRP agonists may, in aspects, be administered in combination, concurrently or sequentially, with conventional treatments for *H. pylori*, gastritis, peptic ulcer disease, or cancer, including antibiotics, anti-inflammatory agents, chemotherapy, hormone therapy, biotherapy, and radiation therapy, for example. The TRP agonists may be formulated together with such conventional treatments when appropriate. For example, the agonists may be administered prior to conventional treatments so that the bacteria are rendered more susceptible to the conventional treatments.

The TRP agonists may be used in any suitable amount, but are typically provided in doses comprising from about 0.001 μM to about 1000 μM agonist, such as from about 0.001 μM, about 0.01 μM, about 0.1 μM, about 1 μM, about 10 μM, or about 100 μM to about 0.01 μM, about 0.1 μM, about 1 μM, about 10 μM, about 100 μM, or about 1000 μM agonist. Alternatively, the TRP agonists may be administered in doses such as from about 0.001 mg/kg to about 1000 mg/kg, such as from about 0.001 mg/kg, about 0.01 mg/kg, about 0.1 mg/kg, about 1 mg/kg, about 10 mg/kg, or about 100 mg/kg to about 0.01 mg/kg, about 0.1 mg/kg, about 1 mg/kg, about 10 mg/kg, about 100 mg/kg, or about 1000 mg/kg.

Additionally, treatment with the compositions described herein may occur once or may be repeated several times. For example, treatment may occur daily, weekly, monthly, yearly, or a combination thereof, depending upon the disease state. For example, a subject may be administered several doses on an hourly, daily, or weekly basis in order to treat an active infection. Once the infection slows or goes into remission, follow-up maintenance doses may be provided, for example, on a monthly basis, every three months, every six months, or on a yearly basis.

The above disclosure generally describes the present invention. A more complete understanding can be obtained by reference to the following specific Examples. These Examples are described solely for purposes of illustration and are not intended to limit the scope of the invention. Changes in form and substitution of equivalents are contemplated as circumstances may suggest or render expedient. Although specific terms have been employed herein, such terms are intended in a descriptive sense and not for purposes of limitation.

EXAMPLES

Example 1—Over-Expression of TRPML1 Rescued VacA-Induced Large Vacuoles

Figure 2:
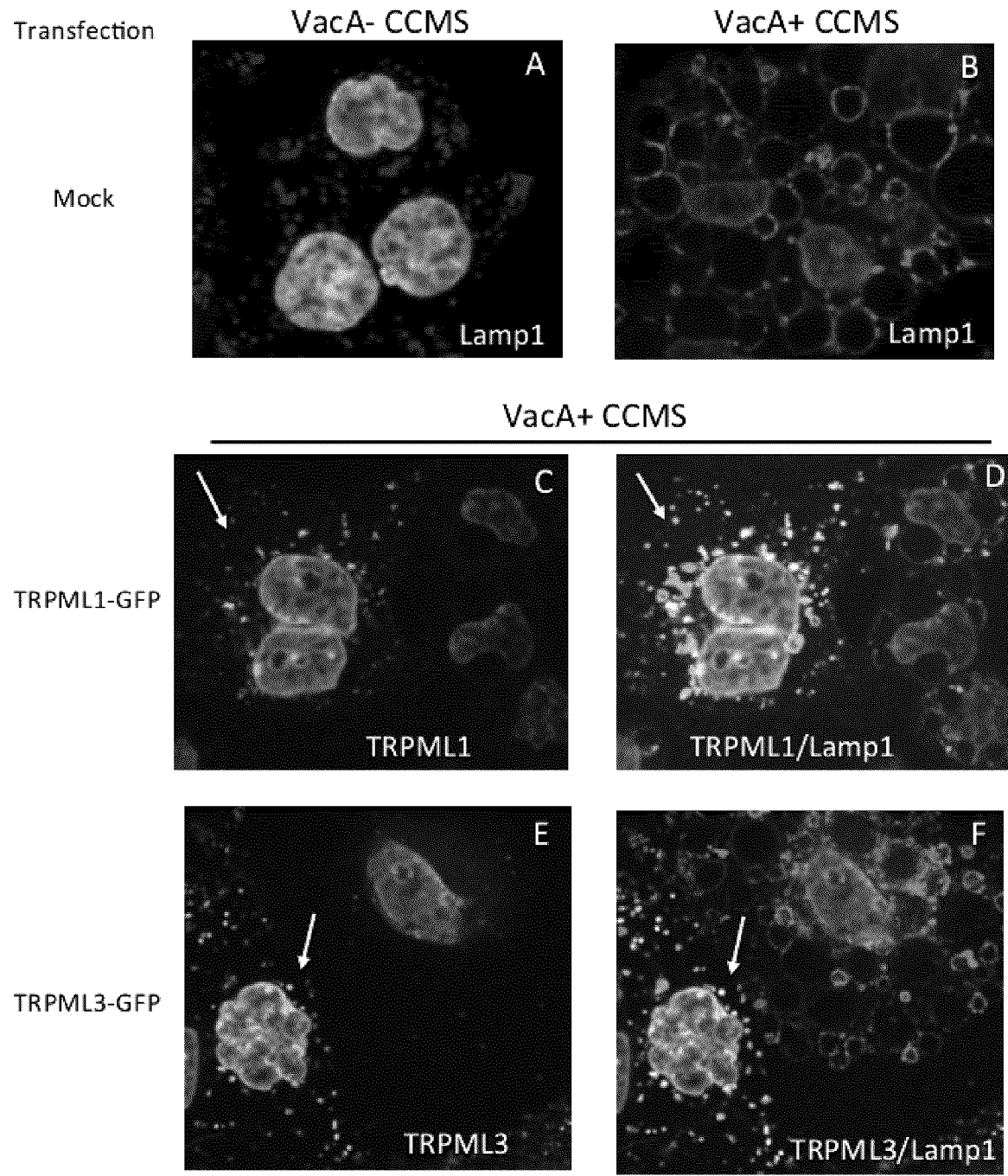
FIG. 2 shows that over-expression of TRPML1 or TRPML3 channels rescues VacA-induced large vacuoles. Gastric epithelial cells (AGS) were transfected with GFP-TRPML1, GFP-TRPML3, or mock transfected as control. Twenty-four hrs after transfection, cells were treated overnight with VacA− or VacA+ conditioned culture media supernatant (CCMS) prior to fixation and staining for Lamp1 (lysosomal associated protein 1) and cell nuclei (using DAPI; a nuclear stain). In mock-transfected, VacA− CCMS treated AGS cells Lamp1 staining shows the normal lysosomal distribution (2A), whereas in the VacA+ CCMS-treated cells Lamp1 delineates the large vacuoles (2B). However, vacuoles were not observed in VacA+-treated cells over-expressing TRPML1 (2 C, D arrow) or TRPML3 (2 E, F arrow) as compared with non-transfected cells within the same population. This experiment was repeated 5 times with similar results.

VacA-treated gastric epithelial (AGS) cells transiently transfected with mCherry-TRPML1 and TRPML3 displayed a significant reduction in vacuole size compared to non-transfected cells within the same population (FIG. 2). These findings illustrate that increased TRPML1 and TRPML3 channel activity via over-expression can directly hinder formation of the specialized intracellular niche wherein *H. pylori* resides. It was next confirmed that VacA specifically targets TRPML1 to promote *H. pylori* survival. Importantly, it was found that reactivating endogenous TRPML1 channels is sufficient to rescue the aforementioned phenotypes.

In the following Examples, a commercially available synthetic TRPML1 agonist, ML-SA1, was used and its capability in restoring the cellular processes disrupted by VacA was assessed.

Example 2—Activation of the TRPML1 Channel Rescues VacA-Induced Vacuolation

Figure 3:
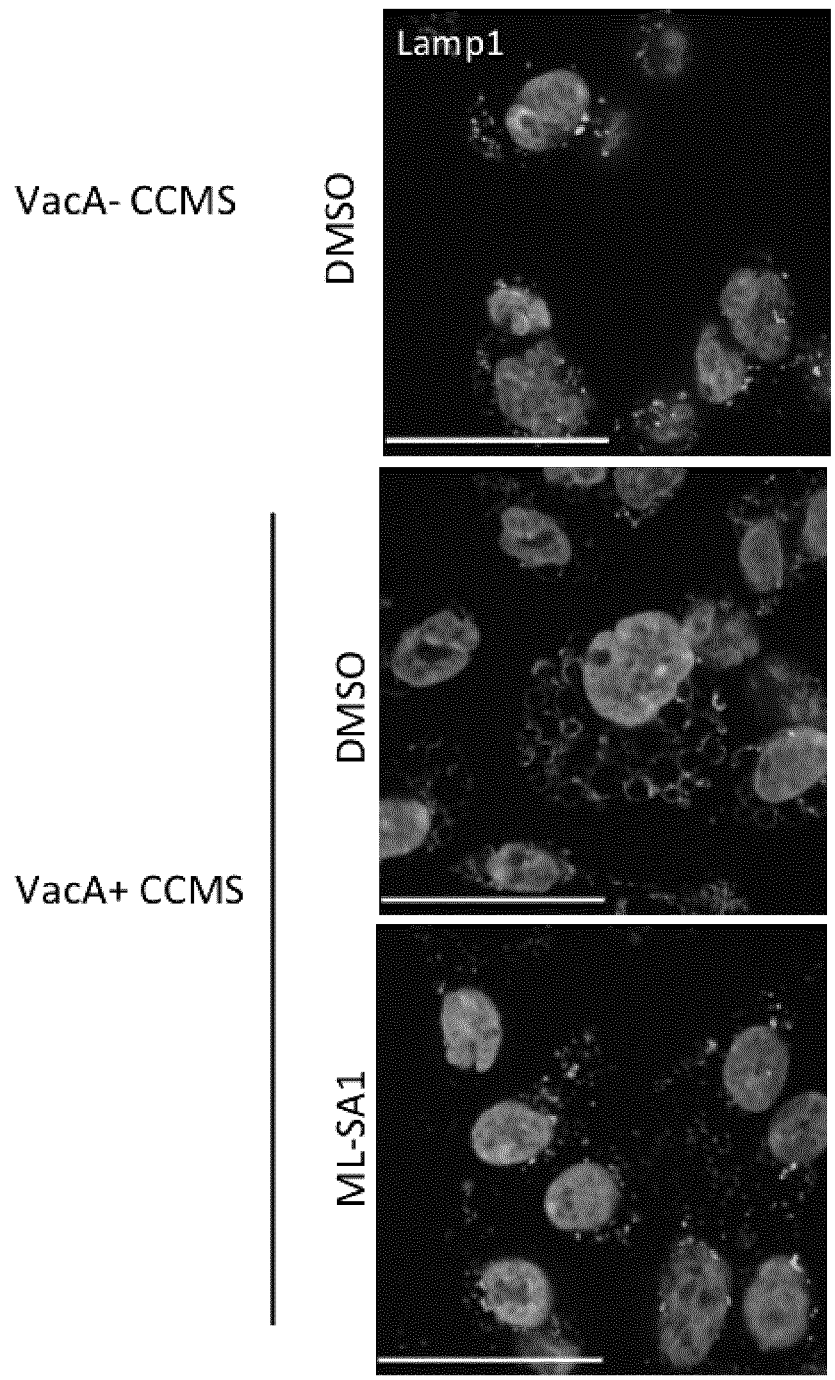
FIG. 3 shows that activation of TRPML1 rescues VacA-induced vacuolation. AGS cells were incubated with CCMS from wild-type (VacA+) or mutant (VacA−) 60190 *H. pylori* for 3 to 4 hrs to induce vacuole formation. Cells were then treated with 20 µM of the TRPML1 agonist ML-SA1 or DMSO (vehicle) for an additional 3 hrs period prior to fixation and staining for Lamp1 and cell nuclei. Treatment with ML-SA1 reversed the vacuolation generated by VacA+ CCMS in AGS cells. Lamp1 staining in these TRPML1 treated cells was indistinguishable from VacA− CCMS control AGS cells. The experiment was repeated 8 times with similar results. One representative experiment is shown.

As shown in FIG. 3, treatment with ML-SA1 reverted the vacuoles generated by VacA in AGS cells. ML-SA1-treated VacA$^+$ AGS cells were indistinguishable from VacA$^-$ control cells, displaying Lamp1 staining that resembled normal lysosome size and distribution.

Example 3—Activation of the TRPML1 Channel Rescued VacA-Disrupted Autophagy

Figure 4:
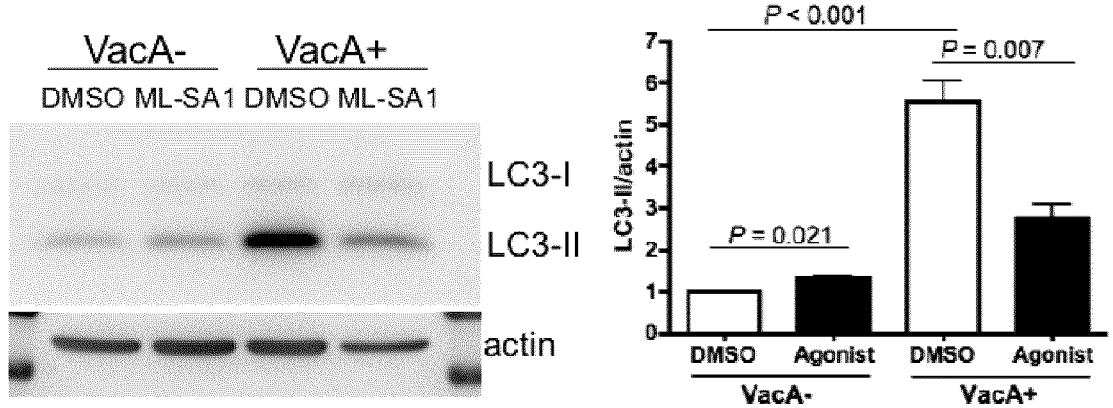
FIG. 4 shows that activation of TRPML1 rescues VacA-disrupted autophagy. AGS cells incubated with VacA+ or VacA− CCMS for 3 to 4 hrs were then treated with 20 µM ML-SA1 or DMSO (vehicle) for an additional 3 hrs. Cell lysates were prepared and probed for the autophagy marker LC3-II and actin (loading control) (4A, left). Densitometry analysis (LC3-II/actin ratio) of 6 experiments is included on the right. VacA+ CCMS-treated AGS cells displayed disrupted autophagy, as shown by the accumulation of LC3-II. However, autophagy was restored by ML-SA1 treatment of cells incubated with VacA+ CCMS, as shown by the reduction in LC3-II. Cells treated as indicated above were fixed and stained for LC3-11 (marker of autophagosomes) and cell nuclei (using DAPI). Consistent with the previous observation, ML-SA1 also reversed the accumulation of dysfunctional autophagosomes (LC3 puncta indicated by arrowheads in 4B) generated by VacA+ CCMS treatment of AGS cells. One representative image of 7 experiments is shown.
Figure 4:
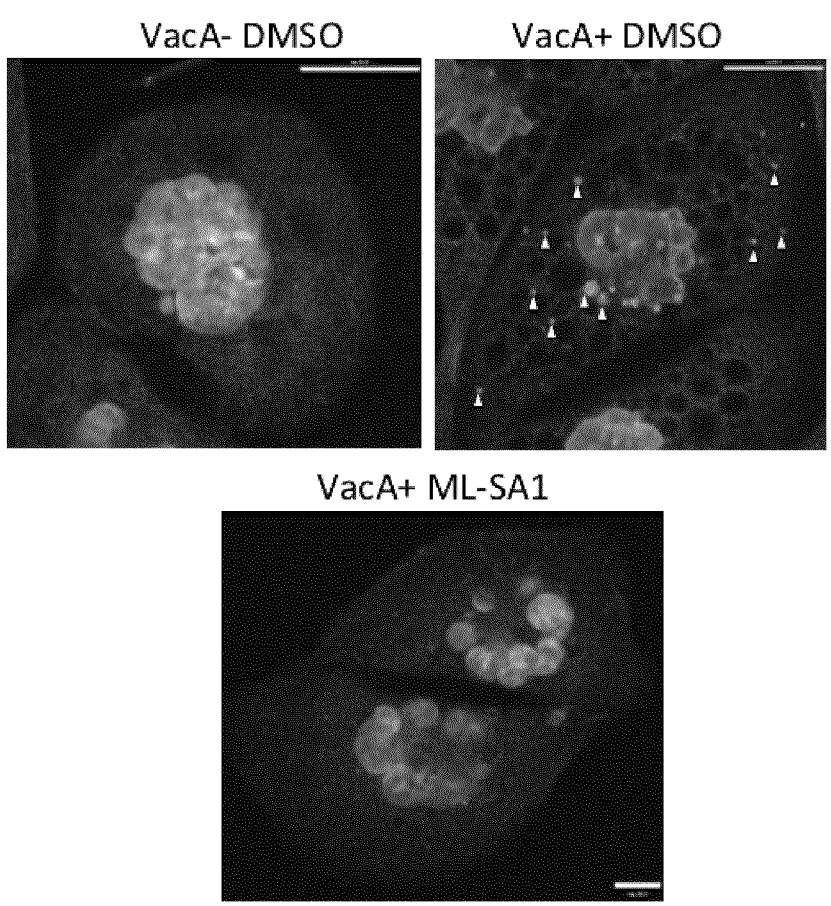

VacA-treated AGS cells exhibited disrupted autophagy, evidenced by the accumulation of LC3-II by immunoblotting (FIG. 4A) and autophagosomes (LC3 puncta) by immunostaining (FIG. 4B). Importantly, it was found that activation of TRPML1 by ML-SA1 significantly restored autophagy in VacA-treated cells (reduced LC3-II and LC3 puncta).

Figure 5:
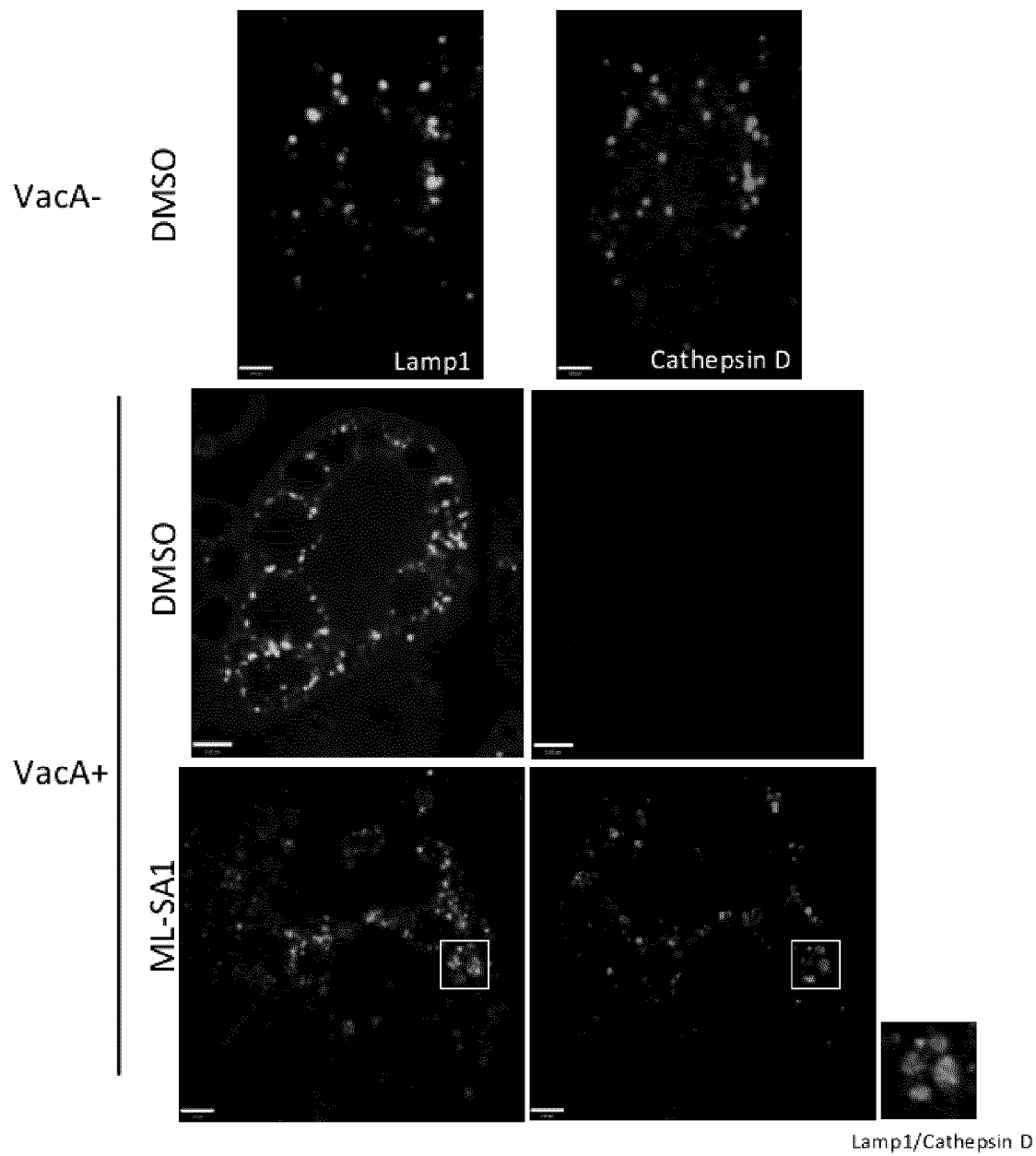
FIG. 5 shows that activation of TRPML1 rescues VacA-induced missorting of cathepsin D. AGS cells were incubated overnight with VacA− or VacA+ CCMS and treated with 20 µM ML-SA1 or DMSO (vehicle) for an additional 4 hrs period prior to fixation and staining for Lamp1 and cathepsin D (one of the lysosome hydrolases). VacA− DMSO treated (control) cells display lysosomes filled with cathepsin D (same puncta obtained by Lamp1 and cathepsin D staining in the top 2 panels) whereas the big vacuoles generated by VacA+ incubation lack cathepsin D (middle panels). ML-SA1 treatment restores cathepsin D sorting to lysosomes, as shown by the presence of cathepsin D in the now smaller vacuoles (bottom panels). A higher magnification of a merged Lamp1/cathepsin D image is included on the right. One representative image of 6 experiments is shown.
Figure 6:
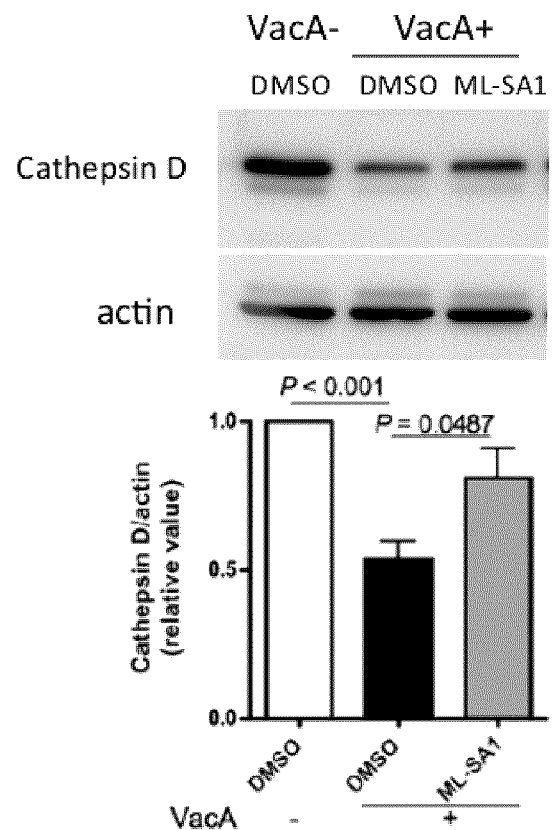
FIG. 6 shows that activation of TRPML1 restores cathepsin D cellular levels in VacA+ CCMS treated cells. AGS cells were incubated overnight with VacA− or VacA+ CCMS and treated with 20 µM ML-SA1 or DMSO (vehicle) for an additional 4 hrs period prior to lysate preparation. Cathepsin D and actin (loading control) levels were analyzed by Western blotting. VacA+ CCMS-treated AGS cells displayed a significant decrease in the cellular levels of cathepsin D, as compared with VacA− CCMS treated (control) cells. Importantly, ML-SA1 administration to the VacA+-treated cells restored cathepsin D levels. One representative blot of 5 is shown (top panel). Densitometry analysis of cathepsin D levels (cathepsin D/actin ratio), normalized to the VacA− treated control is shown (bottom panel).
Figure 7:
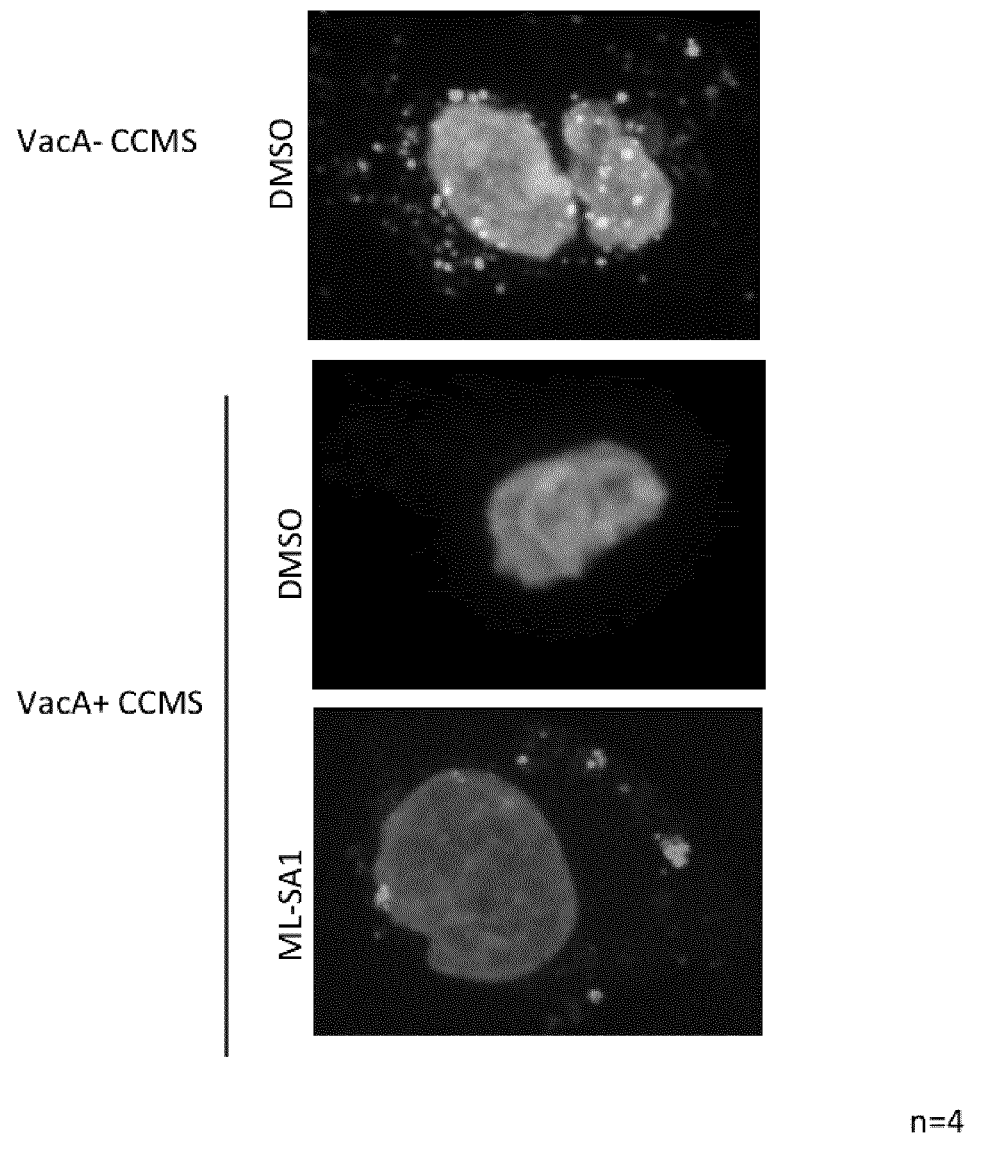
FIG. 7 shows that activation of TRPML1 rescues lysosomal degradative function in VacA+ CCMS treated cells. AGS cells were incubated overnight with VacA− or VacA+ CCMS and treated with 20 µM ML-SA1 or DMSO (vehicle) for an additional 3 hrs period prior to being loaded with red DQ-BSA for an additional 4 hrs. Cells were then fixed and stained with DAPI. Red DQ-BSA is a chromogenic substrate taken up by the cells by endocytosis. The dye generates a fluorescence signal once hydrolyzed in lysosomes. VacA− treated control cells efficiently degrade the substrate resulting in the detection of the fluorescence signal (lysosomal-like white puncta in 7A) whereas in VacA+ treated cells minimal to none fluorescence is detected (7B). ML-SA1 administration restores the degradative capacity of the diminished VacA+ induced vacuoles as demonstrated by the presence of fluorescent signal from degradation of DQ-BSA (white puncta in 7C). The experiment was repeated 4 times with similar results.

Example 5—Activation of TRPML1 Rescued Vesicular Trafficking, Cathepsin D Levels, and Lysosomal Degradative Function ML-SA1 administration to VacA$^+$ treated AGS cells recovered the delivery of cathepsin D to intracellular vacuoles (FIG. 5) and increased cathepsin D cellular levels as detected by immunoblotting (FIG. 6). Importantly, ML-SA1-treated cells also regained the ability to degrade the chromogenic substrate, DQ-BSA (FIG. 7). Altogether, these findings indicate that activation of the TRPML1 channel reverts formation of the VacA-induced non-degradative vacuole.

Figure 8:
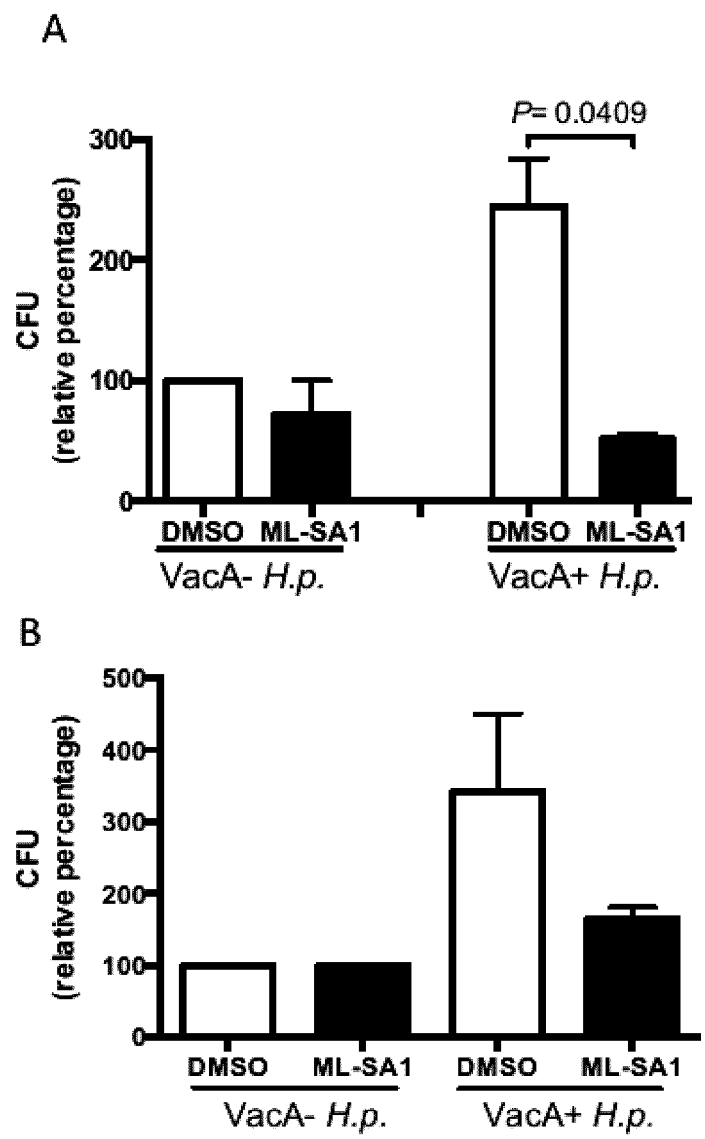
FIG. 8 shows that activation of TRPML1 rescues VacA-promoted intracellular bacteria survival. AGS cells were infected with wild-type (VacA+) or mutant (VacA−) *H. pylori* for 4 hrs followed by washes to remove non-adherent bacteria. The culture media was then supplemented with gentamicin (100 µg/ml) for 1 hr and later reduced to 10 µg/ml for the rest of the assay to prevent extracellular bacterial growth. Total infection time was 8 hrs (top panel), or 24 hrs (bottom panel). ML-SA1 (20 µM) or DMSO (vehicle) was added to the media for the last 3 hrs (top) or 4 hrs (bottom) of the experiment. Intracellular bacteria were retrieved from the infected cells with 1% saponin, serial dilutions prepared and plated in *Brucella* agar for colony forming unit (CFU) determinations. Wild-type (VacA+) *H. pylori* display enhanced intracellular survival compared with the isogenic VacA mutant (VacA−). Incubation with the TRPML1 agonist, ML-SA1, abolished the enhanced survival of the wild-type strain to the VacA− mutant levels. The 8 hrs infection experiment was repeated 4 times whereas the 24 hrs infection was repeated 2 times.
Figure 9:
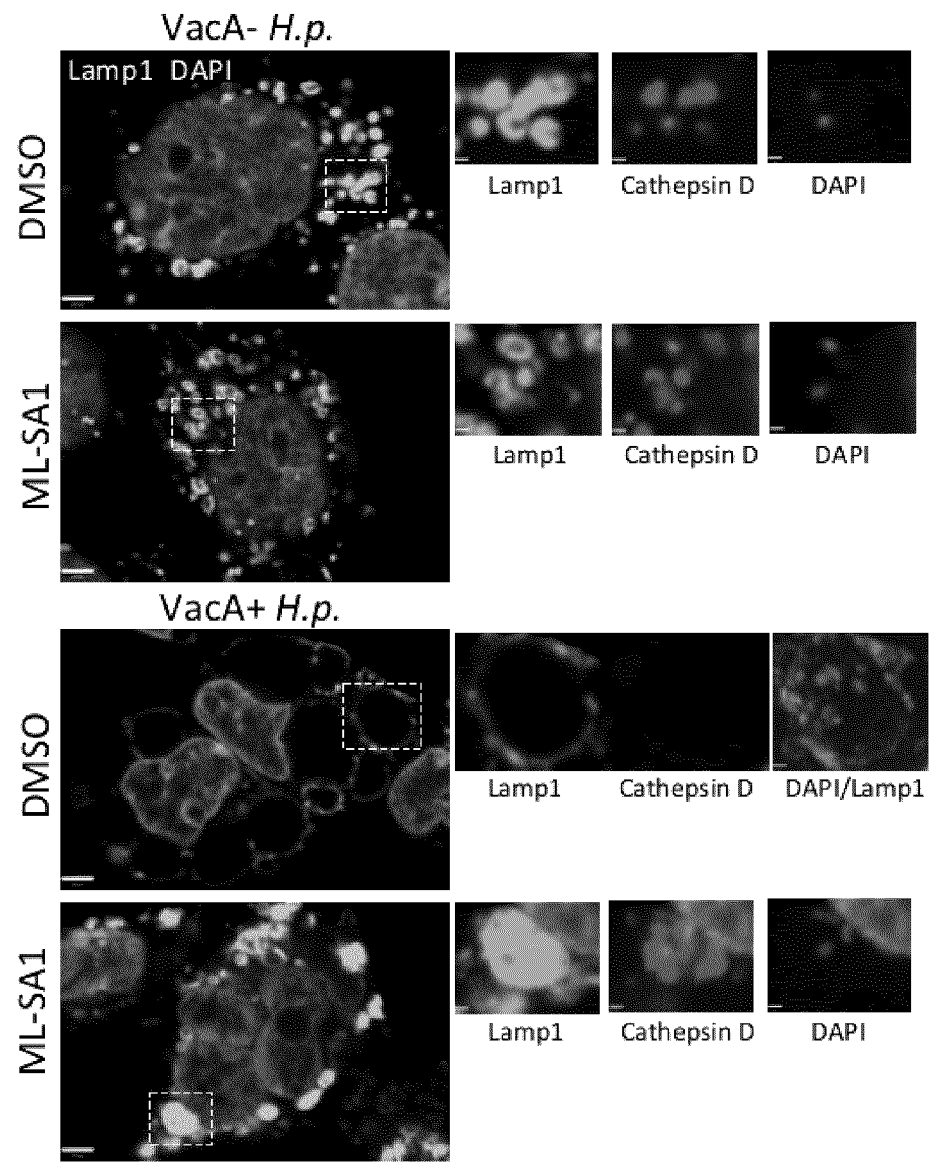
FIG. 9 shows that activation of TRPML1 rescues wild-type (VacA+) *H. pylori* induced vacuolation and missorting of cathepsin D. AGS cells infected with the indicated *H. pylori* were treated with ML-SA1 (or DMSO) for 4 hrs, fixed and stained for Lamp1, cathepsin D and cell nuclei. A merged image is shown on the left, and the individual stainings corresponding to a higher magnification of the selected areas are included on the right. In the AGS cells infected with VacA– *H. pylori* mutant, the cathepsin D-filled lysosomes efficiently killed the intracellular bacteria (visualized by DAPI). In contrast, in VacA+ *H. pylori* infected cells a greater number of bacteria are found in the large vacuoles that lack cathepsin D. Importantly, administration of ML-SA1 causes a reduction in the size of the vacuoles, which now contain the lysosomal hydrolase cathepsin D, comparable to the VacA– *H. pylori* infected cells.

Example 6—Activation of TRPML1 Abolished VacA-Promoted Intracellular Bacteria Survival It was next confirmed that reversion of the formation of the non-degradative, protective vacuole had an impact on intracellular bacteria survival. To this end, AGS cells infected with wild-type (VacA$^+$) or VacA$^-$ mutant *H. pylori* were incubated with the cell-impermeant antibiotic gentamicin to kill extracellular bacteria. Intracellular bacteria were then retrieved and quantified. As shown in FIG. 8, ML-SA1 reverted the enhanced intracellular survival of the wild-type (VacA$^+$) *H. pylori* to the levels of the VacA$^-$ mutant both after short (8 h) or long (24 h) infection times. The big vacuoles, depleted of cathepsin D and filled with bacteria observed in the VacA$^+$ *H. pylori* infected cells (FIG. 9, inset), were reduced in size and filled with the hydrolytic enzyme after ML-SA1 treatment (FIG. 9, inset). Thus, the reduction in intracellular survival was a consequence of the destruction of the VacA$^-$ *H. pylori* protective niche (FIG. 8,9).

Altogether, these Examples clearly establish that increasing the activity of TRPML1 and/or TRPML3 restores VacA-disrupted vesicular trafficking and lysosome function. This leads to the recovery of autophagy and destruction of the protective bacterial niche with the consequent killing of intracellular bacteria. Thus, it has been established that TRPML1 and/or TRPML3 is an effective target for the treatment of the VacA$^+$ *H. pylori* infections. Its activation is expected to reduce the virulence of highly pathogenic VacA$^+$ strains and reduce carcinogenesis.

Figure 10:
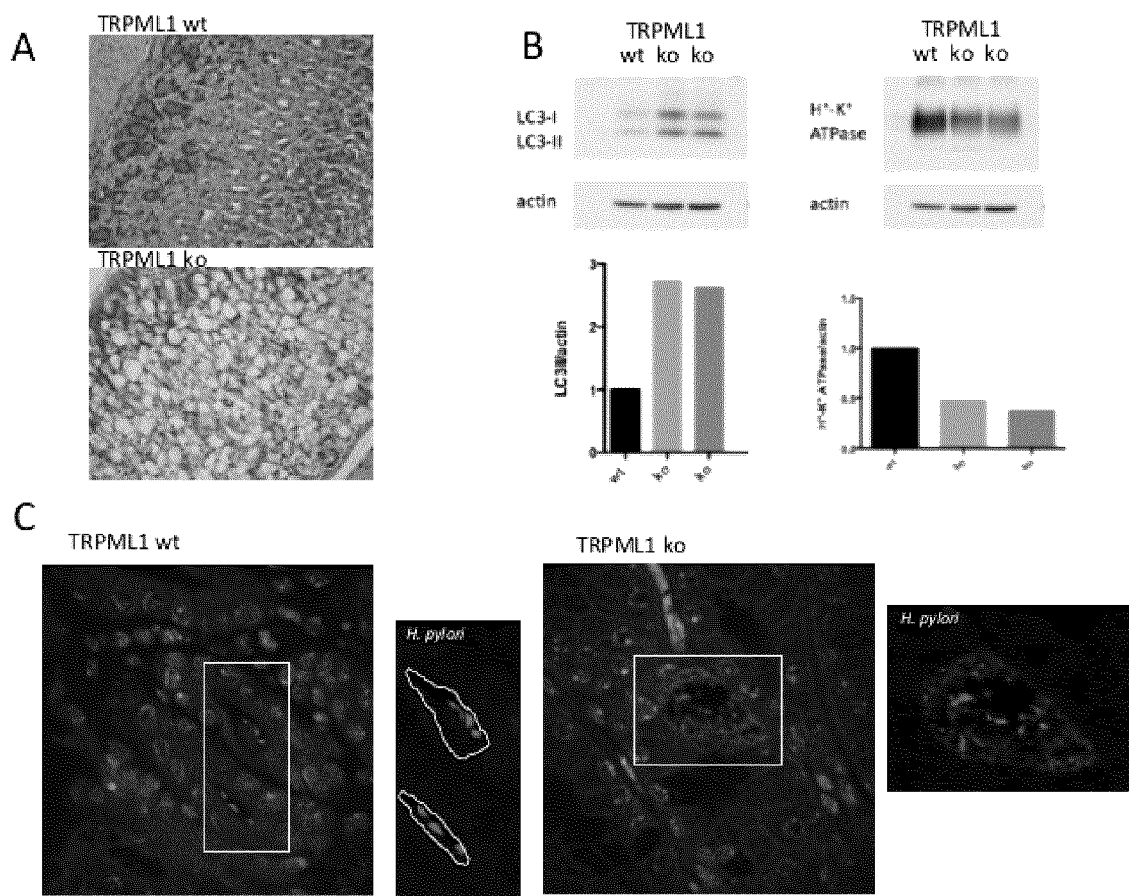
FIG. 10 shows that TRMPL1 deficiency phenocopies the gastric pathology of *H. pylori* (VacA+) infections and promotes intracellular bacteria survival in vivo. To test whether VacA impairs TRPML1 channel activity to promote colonization, the stomachs of TRPML1 knockout (ko) mice and normal littermates (wt) were isolated and it was confirmed that lack of TRPML1 in the stomach produced enlarged vacuoles (10A), disrupted autophagosome maturation (indicated by the increased LC3-II levels) and reduced the levels of the $H^+/K^+$ ATPase (10 B). Next, we the TRPML1 ko mice and wild-type littermates were infected with the murine-adapted strain of *H. pylori* (SS1) that does not express a functional VacA. After a 6-week infection, the stomachs were collected and processed for *H. pylori* staining. *H. pylori* was detected in the lumen of the gastric glands in the wild-type stomachs (10C). In contrast, in the TRPML1-ko stomachs *H. pylori* was found within vacuoles in a protected intracellular niche. Thus it was confirmed that the lack of TRPML1 in the stomach promotes *H. pylori* intracellular survival, mimicking the effects observed with infection in the presence of VacA, which has been shown herein to inhibit TRPML1 activity.

Example 7—TRMPL1 Deficiency Phenocopies the Gastric Pathology of *H. pylori* (VacA+) Infections and Allows Intracellular Bacteria Survival Consistent with the findings above that VacA impairs TRPML1 channel activity to promote colonization, it has now been found that TRPML1 deficiency in vivo causes similar effects as VacA+ *H. pylori* infection. FIG. 10A shows that lack of TRPML1 in the murine stomach produces enlarge vacuoles, disrupts autophagosome maturation (indicated by the increased LC3-II levels) and reduces the levels of the H$^+$/K$^+$ ATPase (FIG. 10 B). Furthermore, TRPML1 knockout mice infected with the murine-adapted strain of *H. pylori* (SS1) that does not express a functional VacA displayed *H. pylori* within vacuoles in a protected intracellular niche whereas *H. pylori* was detected in the lumen of gastric glands in the wild-type stomachs (FIG. 10C). Thus, it has been confirmed that the lack of TRPML1 in the stomach promotes *H. pylori* intracellular survival, mimicking the effects observed with the infection in the presence of VacA.

Figure 11:
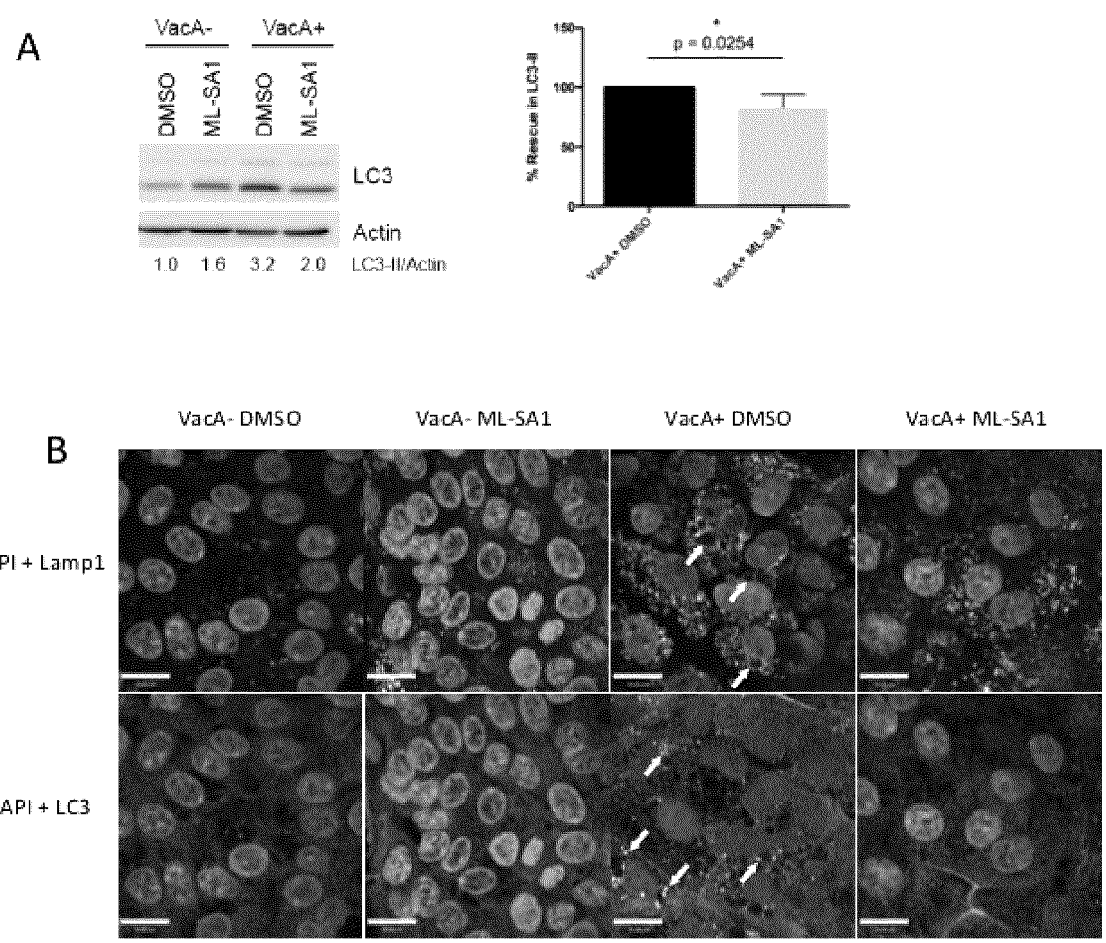
FIG. 11 shows that ML-SA1 rescues large vacuoles and disrupted autophagy caused by VacA. (11A) 3-dimensional human gastric organoids were treated 16 h with VacA– or VacA+ culture supernatant, then 5 h with vehicle (DMSO) or ML-SA1. One representative Western blot is shown and the corresponding quantification of the rescue in LC3-II by treatment with ML-SA1 from organoids derived from 5 different patients. (B) Representative confocal images taken from human gastric organoid monolayers treated for 16 h with VacA– or VacA+ culture supernatant, then 3 h with vehicle (DMSO) or ML-SA1. VacA-induced large vacuoles were visualized by Lamp1, autophagy by LC3 and nuclei by DAPI. Note large Lamp1 positive rings and LC3 puncta (arrows) in VacA+ DMSO that were rescued in VacA+ ML-SA1.

Example 8: Activation of TRPML1 in Human Gastric Organoids Rescued VacA-Induced Large Vacuoles and Disrupted Autophagy Organoids are 3-dimensional primary cell cultures that recapitulate the normal stomach physiology. These cultures are derived from stem cells located in the gastric gland that differentiate into complex structures containing the different cell types found in the stomach epithelium. To ensure findings from the cancerous gastric cell line (AGS) held true in a physiological model, organoids were derived from multiple different patients and treated with VacA. As shown in FIG. 11, treatment of the gastric organoids with VacA caused the formation of large intracellular vacuoles (Lamp1) and disrupted autophagy (LC3). The large vacuoles were reverted and autophagy was restored upon treatment with the TRPML1 agonist, ML-SA1. These findings show that in complex, patient-derived primary cultures, VacA impairs TRPML1 function, which can be rescued by reactivation of the channel.

Figure 12:
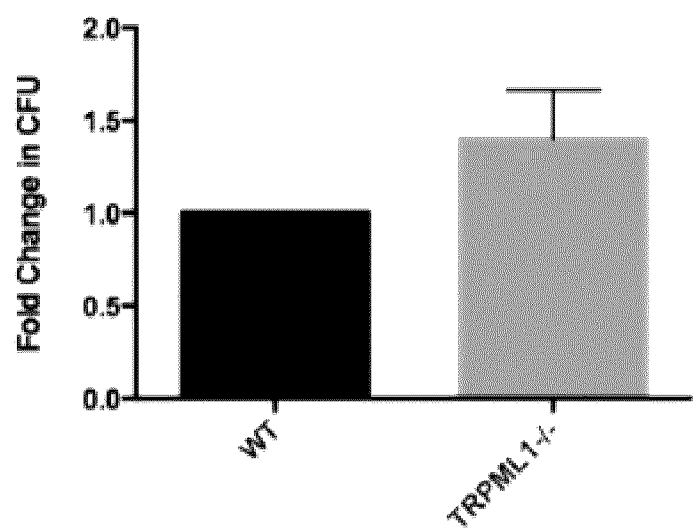
FIG. 12 shows that *H. pylori* exhibits increased intracellular survival in TRPML1 deficient murine gastric organoids. Wildtype (WT) or TRPML1 deficient (TRPML1–/–) murine gastric organoid monolayers were infected with the mouse-adapted *H. pylori* strain, SS1, for 16 h. Cells were incubated with the cell-impermeant antibiotic gentamicin to kill extracellular bacteria. Intracellular bacteria were then retrieved and quantified.

Example 9: *H. Pylori* Exhibits Increased Intracellular Survival in TRPML1 Deficient Murine Gastric Organoids As shown in FIG. 12, wildtype (WT) or TRPML1 deficient (TRPML1-/-) murine gastric organoid monolayers were infected with the mouse-adapted *H. pylori* strain, SS1. Cells were incubated with the cell-impermeant antibiotic gentamicin to kill extracellular bacteria. Intracellular bacteria were then retrieved and quantified. This example utilizes a complex, primary cell model to demonstrate that intracellular pathogens such as *H. pylori* exhibit enhanced intracellular survival in cells with impaired TRMPL1 activity.

Example 10

Figure 13:
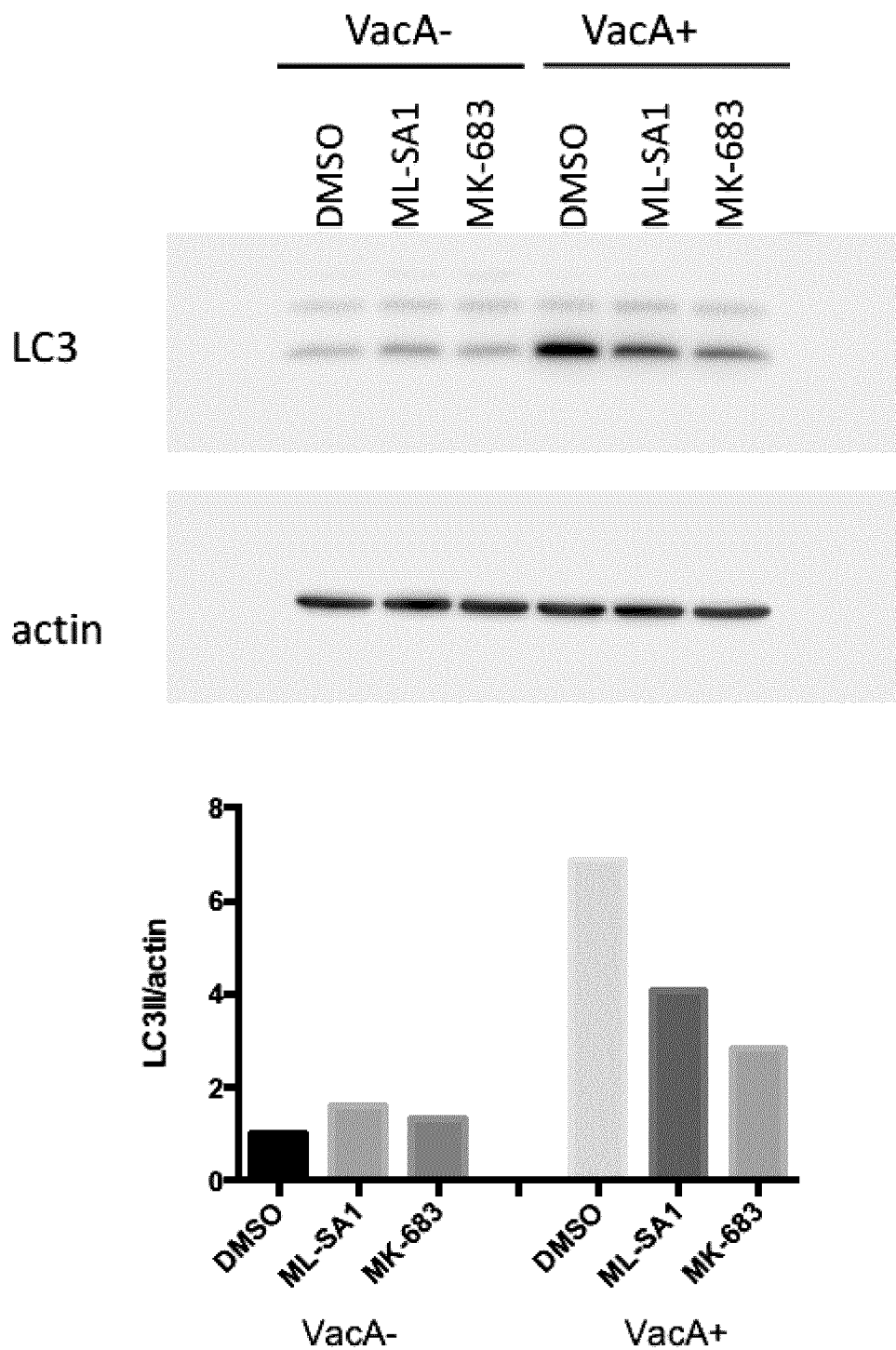
FIG. 13 shows the effect of MK6-83 on restoration of VacA-disrupted autophagy.

To validate the results obtained with ML-SA1 and confirm that VacA impairs TRPML1 activity, a new recently described TRPML1 agonist, MK6-83, was also evaluated in its ability to restore VacA-disrupted autophagy. To this end, AGS cells incubated with VacA+ or VacA– CCMS for 4 hours were treated with 20 μM ML-SA1, 10 μM MK6-83 or DMSO (vehicle) for additional 3 hour period. Cell lysates were prepared and assessed for LC3-II and actin as loading control. As shown in FIG. 13, both ML-SA1 and MK6-83 treatments restored the VacA-disrupted autophagy as shown by the reduction of LC3-II levels, validating that VacA targets TRPML1 to disrupt autophagy. This example provides evidence that various TRPML1 agonists of different structures work in the same way by targeting TRPML1 to restore VacA-disrupted autophagy.

The above disclosure generally describes the present invention. Although specific terms have been employed herein, such terms are intended in a descriptive sense and not for purposes of limitation.

All publications, patents and patent applications cited above are herein incorporated by reference in their entirety to the same extent as if each individual publication, patent or patent application was specifically and individually indicated to be incorporated by reference in its entirety.

Although preferred embodiments of the invention have been described herein in detail, it will be understood by those skilled in the art that variations may be made thereto without departing from the spirit of the invention or the scope of the appended claims.

The invention claimed is:

1. A method for treating and/or preventing a disorder associated with disrupted autophagosome maturation in a subject, the method comprising administering to the subject an agent that promotes autophagosome maturation, wherein the disorder associated with disrupted autophagosome maturation is an infection caused by *H. pylori*, thereby treating and/or preventing the disorder associated with disrupted autophagosome maturation in the subject.

2. The method of claim 1, wherein the *H. pylori* is VacA$^+$.

3. The method of claim 1, wherein the agent is selected from a TRPML1 agonist, a TRPML2 agonist, a TRPML3 agonist, or a combination thereof.

4. The method of claim 3, wherein the agonist is specific for TRPML1 and/or TRPML3.

5. The method of claim 4, wherein the agonist is selected from the group consisting of ML-SA1, SF-22, SF-51, MK6-83, derivatives thereof, prodrugs thereof, analogs thereof, and combinations thereof.

6. The method of claim 1, wherein the agent is administered in combination with an antibiotic.

7. The method of claim 6, wherein the combination shows a synergistic treatment and/or preventative effect.

* * * * *